(12) United States Patent
May et al.

(10) Patent No.: US 11,612,582 B2
(45) Date of Patent: Mar. 28, 2023

(54) GRAPHICAL USER INTERFACES FOR DETERMINING PERSONALIZED ENDOCANNABINOID GENOTYPES AND ASSOCIATED RECOMMENDATIONS

(71) Applicant: Endocanna Health, Inc., Encino, CA (US)

(72) Inventors: Len May, Encino, CA (US); Eric Kaufman, Encino, CA (US)

(73) Assignee: EndoCanna Health, Inc., Burbank, CA (US)

(*) Notice: Subject to any disclaimer, the term of this patent is extended or adjusted under 35 U.S.C. 154(b) by 317 days.

(21) Appl. No.: 16/760,155

(22) PCT Filed: Oct. 30, 2018

(86) PCT No.: PCT/US2018/058168
§ 371 (c)(1),
(2) Date: Apr. 29, 2020

(87) PCT Pub. No.: WO2019/089558
PCT Pub. Date: May 9, 2019

(65) Prior Publication Data
US 2020/0327987 A1 Oct. 15, 2020

Related U.S. Application Data

(60) Provisional application No. 62/721,294, filed on Aug. 22, 2018, provisional application No. 62/680,885, (Continued)

(51) Int. Cl.
*G16H 10/40* (2018.01)
*G16H 10/60* (2018.01)
(Continued)

(52) U.S. Cl.
CPC .......... *A61K 31/352* (2013.01); *A61K 31/015* (2013.01); *A61K 31/05* (2013.01);
(Continued)

(58) Field of Classification Search
None
See application file for complete search history.

(56) References Cited

U.S. PATENT DOCUMENTS

2016/0314251 A1   10/2016  Pratsevall Garcia et al.
2016/0335543 A1*  11/2016  Goldstein .............. G16H 70/00
2020/0372993 A1*  11/2020  Chu ........................ G16H 40/63

FOREIGN PATENT DOCUMENTS

KR   10-2015-0042882 A   4/2015

OTHER PUBLICATIONS

Erickson et al., Cheek swabs, SNP chips, and CNVs: Assessing the quality of copy number variant calls generated with subject-collected mail-in buccal brush DNA samples on a high-density genotyping microarray. BMC Med Genet 13, 51 (2012).https://doi.org/10.1186/1471-2350-13-51 (Year: 2012).*

(Continued)

*Primary Examiner* — Devin C Hein
(74) *Attorney, Agent, or Firm* — Lee Sullivan Shea & Smith LLP

(57) ABSTRACT

An example embodiment may involve (i) receiving, by a server device, deoxyribonucleic acid (DNA) information associated with a user; (ii) parsing, by the server device, the DNA information to identify one or more single nucleotide polymorphisms (SNPs)—(iii) determining, by the server device and based, on the identified SNPs, an endocannabinoid genotype of the user; (iv) determining, based on the endocannabinoid genotype of the user, a recommendation of one or more cannabinoid formulations; (v) transmitting, to a client device associated with the user, a web-based repre- (Continued)

sentation of a first graphical user interface; and (vi) receiving, from the client device, an indication to display a detailed representation of a particular cannabinoid formulation of the one or more cannabinoid formulations.

20 Claims, 15 Drawing Sheets

Related U.S. Application Data filed on Jun. 5, 2018, provisional application No. 62/707,300, filed on Oct. 30, 2017.

(51) Int. Cl.
| | |
|---|---|
| *G16H 15/00* | (2018.01) |
| *G16H 50/70* | (2018.01) |
| *G16H 50/20* | (2018.01) |
| *G16H 70/40* | (2018.01) |
| *G16H 20/10* | (2018.01) |
| *G16B 20/20* | (2019.01) |
| *A61K 31/352* | (2006.01) |
| *A61K 31/015* | (2006.01) |
| *A61K 31/05* | (2006.01) |
| *G06F 3/0484* | (2022.01) |
| *A61K 45/06* | (2006.01) |

(52) U.S. Cl.
CPC .......... *G06F 3/0484* (2013.01); *G16B 20/20* (2019.02); *G16H 10/40* (2018.01); *G16H 10/60* (2018.01); *G16H 15/00* (2018.01); *G16H 20/10* (2018.01); *G16H 50/20* (2018.01); *G16H 50/70* (2018.01); *G16H 70/40* (2018.01); *A61K 45/06* (2013.01)

(56) References Cited

OTHER PUBLICATIONS

Hryhorowicz, Szymon et al., "Pharmacogenetics of Cannabinoids", Eur J Drug Metab Pharmacokinet, vol. 43, May 22, 2017, pp. 1-12.
PCT International Search Report and Written Opinion, PCT International No. PCT/US2018/058168, dated Jan. 17, 2019, 13 pages.
European Search Report, European Patent Application No. 18872556.0, dated Jul. 26, 2021, 14 pages.
Onaivi, Emmanuel S., "Endocannabinoid System, Pharmacogenomics and Response to Therapy", Pharmacogenomics, vol. 11, No. 7, Jul. 1, 2010, pp. 907-910.
Colizzi, Marco et al., "Does Cannabis Composition Matter? Differential Effects of Delta-9-Tetrahydrocannabinol and Cannabidiol on Human Cognition", Current Addiction Reports, vol. 4, No. 2, Apr. 29, 2017, pp. 62-74.

\* cited by examiner

| System Users Table 422 | | | | |
|---|---|---|---|---|
| Show 10 entries | | | Search: | +Add Record / CReload |
| Last Name | First Name | Email (login) | Permissions | Action |
| Smith | Harrison | user1@gmail.com | admin | Edit Delete |
| Jones | Kevin | user2@gmail.com | member | Edit Delete |
| Hayes | Ricky | user3@gmail.com | member | Edit Delete |
| Johnson | Terrance | user4@gmail.com | member | Edit Delete |
| Williams | Michelle | user5@gmail.com | admin member | Edit Delete |
| Simpson | Katie | user6@gmail.com | admin | Edit Delete |
| Fry | Phillip | user7@gmail.com | member | Edit Delete |
| Kennedy | John | user8@gmail.com | admin member | Edit Delete |
| Scott | William | user9@gmail.com | member | Edit Delete |
| Taylor | Jason | user10@gmail.com | member | Edit Delete |
| Last Name | First Name | Email (login) | Permissions | Action |
| Showing 1 to 10 of 11 entries | | | | Previous 1 2 Next |

FIG. 4B

ENDOCANNA HEALTH ≡ Search...

Registered Kits 430

Show [10 ▼] entries | +Add Record ⟳Reload | Search: [ ]

| Name 432 | Email | Phone | Barcode | Status | Created On | Action |
|---|---|---|---|---|---|---|
| Smith, Harrison | user1@gmail.com | (555) 123-3456 | 1874-785641 | registered | 2018-08-09 06:41 AM | Upload Results |
| Jones, Kevin | user2@gmail.com | (555) 555-3456 | 1004-784441 | registered | 2018-08-09 04:19 PM | Upload Results |
| Hayes, Ricky | user3@gmail.com | (555) 123-1234 | 7894-711474 | registered | 2018-08-13 12:10 PM | Upload Results |
| Johnson, Terr. | user4@gmail.com | (555) 123-8794 | 9673-478246 | registered | 2018-08-13 02:39 PM | Upload Results |
| Williams, Mich. | user5@gmail.com | (555) 789-7897 | 0147-078056 | registered | 2018-08-13 05:44 PM | Upload Results |
| Simpson, Katie | user6@gmail.com | (555) 186-7482 | 7513-784614 | registered | 2018-08-14 08:03 AM | Upload Results |
| Fry, Phillip | user7@gmail.com | (555) 972-7861 | 1476-784124 | registered | 2018-08-14 08:09 AM | Upload Results |
| Kennedy, John | user8@gmail.com | (555) 427-7913 | 7345-781496 | registered | 2018-08-14 08:56 AM | Upload Results |
| Scott, William | user9@gmail.com | (555) 858-6006 | 7425-789142 | registered | 2018-08-14 02:05 PM | Upload Results |
| Taylor, Jason | user10@gmail.com | (555) 312-1234 | 8742-123794 | registered | 2018-08-14 04:20 PM | Upload Results |
| Status | | | | | Created On | Action |

Showing 1 to 10 of 16 (filtered from 39 total entries)     Previous [1] [2] Next

FIG. 4C

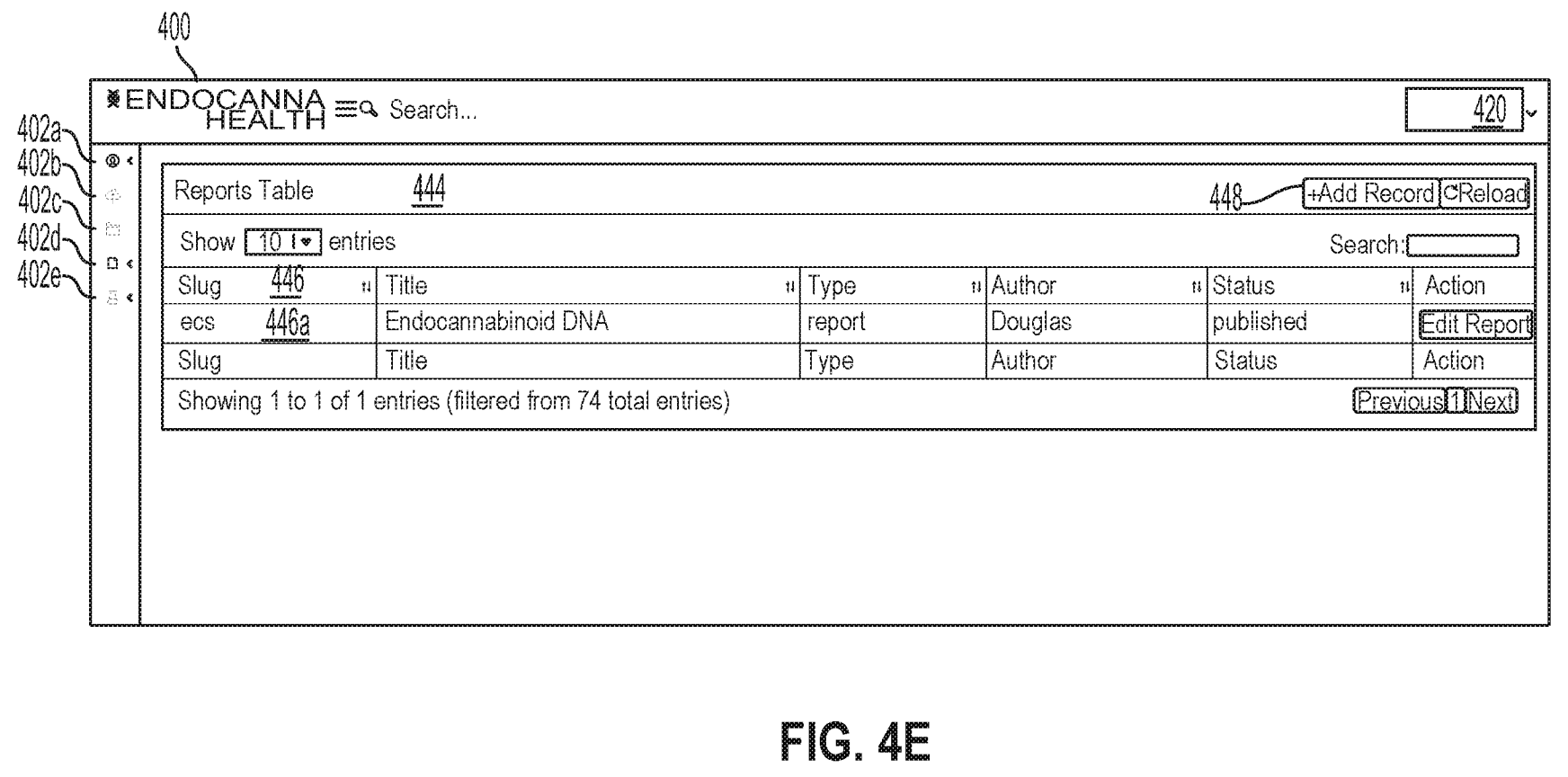

| | | Reports Table | | | | 420 |
|---|---|---|---|---|---|---|
| | | Show 10 ▾ entries 444 | | | +Add Record \| ⟳Reload | |
| | | | | | Search: 448 | |
| | | Slug 446 | ⇅ Title | ⇅ Type | ⇅ Author | ⇅ Status | ⇅ Action |
| | | ecs 446a | Endocannabinoid DNA | report | Douglas | published | Edit Report |
| | | Slug | Title | Type | Author | Status | Action |
| | | Showing 1 to 1 of 1 entries (filtered from 74 total entries) | | | | Previous 1 Next |

FIG. 4E

| Pages Table | | | | 450 | +Add Record | CReload |
|---|---|---|---|---|---|---|
| Show 10 entries | | | | | Search: | |
| Parent 452 | Title | Page Type | Status | Updated On | Action | |
| none | Terms of Service | report_detail | published | 07/29/2018 | Edit | Delete |
| none | Health Reports Agreement | info | published | 07/25/2018 | Edit | Delete |
| none | Privacy Policy | info | published | 08/08/2018 | Edit | Delete |
| none | Welcome To Your Cannabinoid DNA Variant Report | report_detail | published | 07/29/2018 | Edit | Delete |
| ecs | Your Endocannabinoid DNA Report Summary | report_detail | published | 08/08/2018 | Edit | Delete |
| ecs | ECS Bipolar | report_summary | published | 07/29/2018 | Edit | Delete |
| none | DNA 101 | report_detail | published | 07/29/2018 | Edit | Delete |
| ecs | ECS Cognitive Function | article | published | 08/04/2018 | Edit | Delete |
| none | How can you benefit from understanding your Endocannabinoid genetics? | article | published | 08/08/2018 | Edit | Delete |
| Parent | Title | Page Type | Status | Updated On | Action | |
| Showing 1 to 10 of 23 entries (filtered from 74 total entries) | | | | Previous 1 2 3 Next | | |

FIG. 4F

| Sections Table 458 | | | | | |
|---|---|---|---|---|---|
| Show 10 entries | | | | +Add Record\|CReload 462 | |
| | | | | Search: | |
| Parent 460 | Slug | Page Type | Status | Updated On | Action |
| ecs_anxiety | ecs_anxiety_5-HTTLPR | section | published | 08/06/2018 | Edit\|Delete |
| ecs_anxiety | ecs_anxiety_rs1049353 | section | published | 08/05/2018 | Edit\|Delete |
| ecs_anxiety | ecs_anxiety_rs324420 | section | published | 08/06/2018 | Edit\|Delete |
| ecs_bipolar | ecs_bipolar_rs41311993 | section | published | 08/06/2018 | Edit\|Delete |
| ecs_cognitive | ecs_cognitive_rs1049353 | section | published | 08/05/2018 | Edit\|Delete |
| ecs_cognitive | ecs_cognitive_rs4680 | section | published | — | Edit\|Delete |
| ecs_cognitive | ecs_cognitive_rs4680b | section | published | — | Edit\|Delete |
| ecs_cognitive | ecs_cognitive_rs12199654 | section | published | — | Edit\|Delete |
| ecs_cognitive | ecs_cognitive_rs7634206 | section | published | — | Edit\|Delete |
| ecs_cognitive | ecs_cognitive_5-HTTLPR | section | published | — | Edit\|Delete |
| Parent | Slug | Page Type | Status | Updated On | Action |
| Showing 1 to 10 of 50 entries (filtered from 74 total entries) | | | | Previous 1 2 3 4 5 Next | |

FIG. 4G

| User Raw Data 466 | | |
|---|---|---|
| Show 10 ▾ entries 468 | | Search: |
| User | Filename | Last Processed | Action |
| Smith | 18237847819.txt | 2018-08-14 09:55:38 | ⚡Process File |
| Jones | 29035798287.txt | 2018-08-16 08:17:12 | ⚡Process File |
| Hayes | 387123487s2.txt | 2018-08-15 15:39:31 | ⚡Process File |
| Johnson | 4zjhxf891da2.txt | 2018-08-13 15:34:30 | ⚡Process File |
| Williams | 5zjhxf8923jad.txt | 2018-08-13 17:09:32 | ⚡Process File |
| Simpson | 238uyfa61z34.txt | 2018-08-12 14:04:56 | ⚡Process File |
| Fry | Jhksdf81fj28s.txt | 2018-08-13 20:48:24 | ⚡Process File |
| Kennedy | 8d87fwq8d5a.txt | 2018-08-11 10:34:44 | ⚡Process File |
| Scott | 834f6sdf7225.txt | 2018-08-13 15:27:09 | ⚡Process File |
| Taylor | 8914dh214d1.txt | 2018-08-13 21:22:12 | ⚡Process File |
| User | Filename | Last Processed | Action |
| Showing 1 to 10 of 10 entries | | | Previous 1 Next |

Search field: 470 ⚡Batch All Now

ENDOCANNA HEALTH

502 — HOME | REPORTS ⌄ | WELLNESS PLANS ⌄ | ARTICLES ⌄ | Demo User — 506

Your Endocannibinoid DNA Report Summary

🖨 Print Summary

*The Endocannibinoid DNA Variant Report* provides you with relevant genetic results to aid in guiding your experience with cannabis. Our mission is to further the research of Endocannibinoid genetics and document the efficacy of medical cannabis. As a member of Endocanna Health, you will receive regular updates to your report as new research becomes available. In addition, you will receive notification via email as new updates become available.

This report summarizes any association in your specific genetic results (genotypes) that may impact your Endocannabinoid system and your cannabis use. The report is divided into sections or mini-reports, organized by trait. Click on the link provided in each summary to review that section.

A red arrow indicates that one or more variances may be flagged for you to review. It is important to note that even if you have an allele combination that is flagged as a variance, this trait may never present itself or be expressed. Please consult a genetic counselor or your medical advisor for more information. If you have any questions or need help locating genetic counseling, please contact us and we will provide you with additional resources.

510 — 🧠 *Mental Health & Wellness*

| | | |
|---|---|---|
| ↑ Anxiety | You may have a greater risk of especially anxiety (in a threatening situation) relative to other genotypes. Please consume responsibly and consult with a specialist for guidance.<br>*View Full Report >>* | 512 |
| ↑ Bi-Polar | This polymorphism was associated with the risk for developing bipolar disorder. A bipolar disorder can include having intense emotional/mood changes (e.g., from sadness/depression/feeling worthless, suicidal thoughts to great optimism/or irritableness/flight of ideas, pacing, handwriting, talking fast, danger seeking behavior, etc. in short order) which profoundly affects one's daily life. Please consume responsibly and consult with a specialist for guidance.<br>*View Full Report >>* | 514 |
| ↑ Cognitive Function | You may experience higher than average impairments to cognitive functions including: how the brain engages in being attentive in complex situations; executive abilities (such as organizing and planning), learning/memory; language; how we perceive our visual environments; and how we understand and respond to social situations when consuming cannabis. Please consume responsibly and consult with a specialist for guidance.<br>*View Full Report >>* | 516 |

FIG. 5B

GRAPHICAL USER INTERFACES FOR DETERMINING PERSONALIZED ENDOCANNABINOID GENOTYPES AND ASSOCIATED RECOMMENDATIONS

CROSS-REFERENCE TO RELATED APPLICATIONS

This application claims the benefit of International Application No. PCT/US2018/058168, filed Oct. 30, 2018, which claims the benefit of U.S. Provisional Application No. 62/707,300, filed Oct. 30, 2017, U.S. Provisional Application No. 62/680,885, filed Jun. 5, 2018, and U.S. Provisional Application No. 62/721,294, filed Aug. 22, 2018, the disclosures of each of which are explicitly incorporated by reference herein in their entirety.

BACKGROUND

Medical use of *cannabis* and associated phytocannabinoids is becoming widely accepted in the United States as an alternative form of medicine. Many states have legalized its use for qualified medical conditions such as chronic pain, epilepsy, sleep disorders, anxiety, cancer, glaucoma, nausea, ALS, Alzheimer's disease, Crohn's disease, Post-traumatic Stress Disorder (PTSD), arthritis, fibromyalgia, and others. Every individual has an endocannabinoid system comprised of chemical receptors in the brain, immune system and central nervous system (for example, cannabinoid receptors CB1 and CB2).

Single nucleotide polymorphisms (SNPs) are stable genetic markers throughout the human genome, which can be tested for their association with various disease traits. These markers can also be associated with various traits that can determine an individual's sensitivity to certain compounds present in *cannabis* such as cannabinoids, terpenes, nitrogenous compounds, flavonoids, non-cannabinoid phenols and other miscellaneous chemical constituents. These endogenous endocannabinoid SNP markers can be tested in a patient and used as biomarkers that may predict how a patient will react or respond to the metabolism of compounds such as delta-9-THC, cannabidiol, other cannabinoids, and terpenoids found in *cannabis*. Furthermore, these biomarkers may suggest the best modality of treatment based on an individual's genetic profile and presence of specific enzymes or lack thereof that may result in negative side-effects from these compounds.

SUMMARY

Deoxyribonucleic acid (DNA) testing has become more common and pervasive in society. Companies such as 23ANDME® and ANCESTRY.COM® offer DNA testing kits that are shipped to individuals eager to find out more information about their genome, including whether they have particular genetic markers that indicate a likelihood of disease, or to determine what area of the world their ancestors inhabited.

This thirst for knowledge has also expanded into using DNA data to determine methods of treatment for certain conditions. For example, DNA data can be used to identify genetic markers indicating how an individual will react to particular substances (e.g., various cannabinoid substances), and which substances will be more or less effective for treating various conditions. These genetic markers are referred to as single nucleotide polymorphisms (SNPs).

Based on an individual's SNPs, a medical provider can determine that individual's endocannabinoid genotype. An endocannabinoid genotype is an individual's genotype as related to the SNPs most relevant to how the individual will react to particular cannabinoid formulations.

Once the individual's endocannabinoid genotype is determined, a recommendation for one or more cannabinoid formulations can be made. The recommendation is based on research regarding how a user's genotype is likely to interact with certain polymorphisms when using *cannabis*.

One prevalent issue after determining an individual's endocannabinoid genotype is how to effectively present the genetic information and recommendation of cannabinoid formulations to the individual. This issue is present due to the technical nature of the DNA information (e.g., SNPs and endocannabinoid genotype) and the disparity in educational levels between the provider and the individual. To bridge this gap in knowledge and expertise, the provider may present the information in the form of a web-based graphical user interface. The graphical user interface may be configurable to display information related to the individual's endocannabinoid genotype. Specifically, the graphical user interface may allow the individual to learn more about their endocannabinoid genotype by reading about the different types of SNPs and their effect when presented with various cannabinoid formulations.

Accordingly, in a first example embodiment, a method may include receiving, by a server device, DNA information associated with a user. The method may further include parsing, by the server device, the DNA information to identify one or more SNPs. The method may also include determining, by the server device and based on the identified SNPs, an endocannabinoid genotype of the user. The method may also include determining, based on the endocannabinoid genotype of the user, a recommendation of one or more cannabinoid formulations. The method may further include transmitting, to a client device associated with the user, a web-based representation of a first graphical user interface, wherein the first graphical user interface is configurable to display information related to the user, wherein the information includes the one or more recommended cannabinoid formulations related to the endocannabinoid genotype of the user.

The method may also include receiving, from the client device, an indication to display a detailed representation of a particular cannabinoid formulation of the one or more cannabinoid formulations. The method may also include transmitting, to the client device, a web-based representation of a second graphical user interface, wherein the second graphical user interface is configurable to display (i) a textual description of the particular cannabinoid formulation, (ii) a textual description of an interaction between the particular cannabinoid formulation and the endocannabinoid genotype of the user, and (iii) a cannabidiol (CBD) to tetrahydrocannabinol (THC) ratio present in the particular cannabinoid formulation.

In a second example embodiment, an article of manufacture may include a non-transitory computer-readable medium, having stored thereon program instructions that, upon execution by a computing system, cause the computing system to perform operations in accordance with the first example embodiment.

In a third example embodiment, a computing system may include at least one processor, as well as memory and program instructions. The program instructions may be stored in the memory, and upon execution by the at least one processor, cause the computing system to perform operations in accordance with the first example embodiment.

In a fourth example embodiment, a system may include various means for carrying out each of the operations of the first example embodiment.

These as well as other embodiments, aspects, advantages, and alternatives will become apparent to those of ordinary skill in the art by reading the following detailed description, with reference where appropriate to the accompanying drawings. Further, this summary and other descriptions and figures provided herein are intended to illustrate embodiments by way of example only and, as such, that numerous variations are possible. For instance, structural elements and process steps can be rearranged, combined, distributed, eliminated, or otherwise changed, while remaining within the scope of the embodiments as claimed.

BRIEF DESCRIPTION OF THE DRAWINGS

FIG. 4B depicts a graphical user interface also showing DNA information at the DNA information provider view, in accordance with example embodiments.

FIG. 4C depicts a graphical user interface also showing DNA information at the DNA information provider view, in accordance with example embodiments.

FIG. 4E depicts a graphical user interface also showing DNA information at the DNA information provider view, in accordance with example embodiments.

FIG. 4F depicts a graphical user interface also showing DNA information at the DNA information provider view, in accordance with example embodiments.

FIG. 4G depicts a graphical user interface also showing DNA information at the DNA information provider view, in accordance with example embodiments.

FIG. 4H depicts a graphical user interface also showing DNA information at the DNA information provider view, in accordance with example embodiments.

FIG. 5B depicts a graphical user interface also showing DNA information at the end-user view, in accordance with example embodiments.

DETAILED DESCRIPTION

Figure 1:
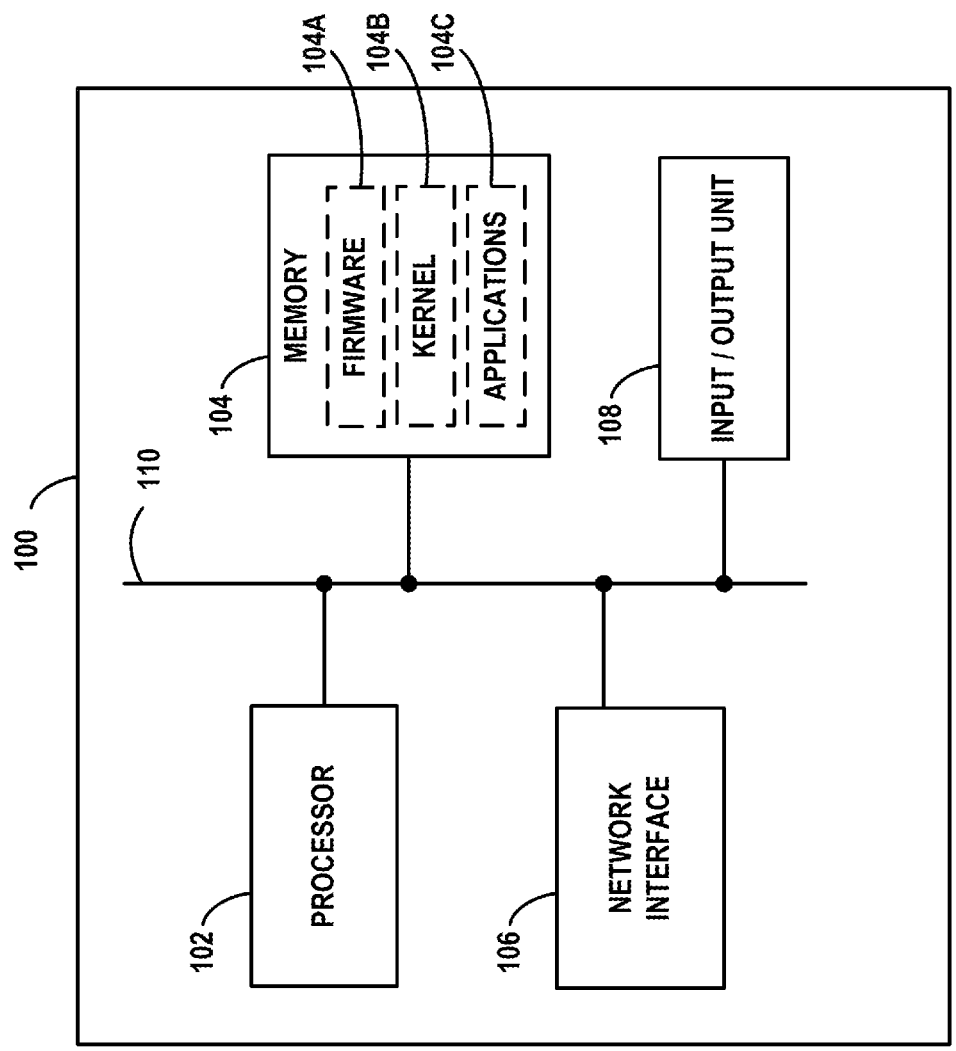
FIG. 1 illustrates a schematic drawing of a computing device, in accordance with example embodiments.

Example methods, devices, and systems are described herein. It should be understood that the words "example" and "exemplary" are used herein to mean "serving as an example, instance, or illustration." Any embodiment or feature described herein as being an "example" or "exemplary" is not necessarily to be construed as preferred or advantageous over other embodiments or features unless stated as such. Thus, other embodiments can be utilized and other changes can be made without departing from the scope of the subject matter presented herein.

Accordingly, the example embodiments described herein are not meant to be limiting. It will be readily understood that the aspects of the present disclosure, as generally described herein, and illustrated in the figures, can be arranged, substituted, combined, separated, and designed in a wide variety of different configurations. For example, the separation of features into "client" and "server" components may occur in a number of ways.

Further, unless context suggests otherwise, the features illustrated in each of the figures may be used in combination with one another. Thus, the figures should be generally viewed as component aspects of one or more overall embodiments, with the understanding that not all illustrated features are necessary for each embodiment.

Additionally, any enumeration of elements, blocks, or steps in this specification or the claims is for purposes of clarity. Thus, such enumeration should not be interpreted to require or imply that these elements, blocks, or steps adhere to a particular arrangement or are carried out in a particular order.

I. INTRODUCTION

Individuals may send their DNA information to various providers with the hope of learning something about themselves, which may include the desire to know where their ancestors inhabited the Earth, whether they are susceptible to certain cancers or diseases, or whether they may react positively or negatively to certain compounds when undergoing treatments for a variety of illnesses. Each provider may determine this information by testing particular parts of the individual's genome. These particular parts of the genome are genetic markers referred to as single nucleotide polymorphisms (SNPs). The SNPs can be tested for their association with various disease traits or to determine how an individual will react to particular compounds. For example, if an individual is determined to have heterozygous alleles (C/T) at the rs1049353 polymorphism of the CNR1 gene, the individual may have reduced focus when using *cannabis*.

Providers that handle DNA information may receive the DNA information in a variety of ways, which can include sending out proprietary DNA test kits or receiving DNA information collected from a third-party service. However, once the DNA information for an individual is obtained, the provider may have problems conveying the information to the individual (i.e., explaining why the individual's genotype indicates that a reaction may occur when ingesting different types of cannabinoid formulations).

The embodiments herein support methods, devices, and systems for providing a more complete view of an individual's genetic information with respect to potential interactions with various cannabinoid formulations. These embodiments enable the collection and analysis of DNA from various sources to provide an individual with detailed information about how cannabinoids may affect their mental and physical health and wellness. With this information, individuals can confidently use certain cannabinoids without the need for experimentation. This information also allows individuals to avoid certain cannabinoids that may cause negative side effects.

Particularly, the embodiments herein describe interactive graphical user interfaces, possibly in the form of webpages, which educate an individual regarding the different genetic markers and why cannabinoids can cause positive or negative effects when those markers are present. For instance, if an individual is determined to have homozygous alleles (C/C) at the rs324420 of the FAAH gene, the individual may have more pain sensitivity to colder temperatures and more need for analgesia during periods of acute pain, such as after an operation. The individual may then use this information to search for a particular cannabinoid formulation that focuses on pain relief.

In this way, the individual may be able to effectively choose the most appropriate cannabinoid formulation for a variety of different circumstances. This may be beneficial as it eliminates the need for an individual to self-treat via a prolonged trial-and-error process.

While the embodiments herein are described as providing web-based interfaces, other types of interfaces may be used instead. For instance, any of the web-based interfaces herein may be replaced by interfaces of standalone applications for personal computers, tablets, smartphones, etc.

Regardless of how they may be implemented, the embodiments herein may make use of one or more computing devices. These computing devices may include, for example, client devices under the control of users, and server devices that directly or indirectly interact with the client devices. Such devices are described in the following section.

II. EXAMPLE COMPETING DEVICES AD CLOUD-BASED COMPUTING ENVIRONMENTS

FIG. 1 is a simplified block diagram exemplifying a computing device 100, illustrating some of the components that could be included in a computing device arranged to operate in accordance with the embodiments herein. Computing device 100 could be a client device (e.g., a device actively operated by a user), a server device (e.g., a device that provides computational services to client devices), or some other type of computational platform. Some server devices may operate as client devices from time to time in order to perform particular operations, and some client devices may incorporate server features.

In this example, computing device 100 includes processor 102, memory 104, network interface 106, and an input/output unit 108, all of which may be coupled by a system bus 110 or a similar mechanism. In some embodiments, computing device 100 may include other components and/or peripheral devices (e.g., detachable storage, printers, and so on).

Processor 102 may be one or more of any type of computer processing element, such as a central processing unit (CPU), a co-processor (e.g., a mathematics, graphics, or encryption co-processor), a digital signal processor (DSP), a network processor, and/or a form of integrated circuit or controller that performs processor operations. In some cases, processor 102 may be one or more single-core processors. In other cases, processor 102 may be one or more multi-core processors with multiple independent processing units. Processor 102 may also include register memory for temporarily storing instructions being executed and related data, as well as cache memory for temporarily storing recently-used instructions and data.

Memory 104 may be any form of computer-usable memory, including but not limited to random access memory (RAM), read-only memory (ROM), and non-volatile memory (e.g., flash memory, hard disk drives, solid state drives, compact discs (CDs), digital video discs (DVDs), and/or tape storage). Thus, memory 104 represents both main memory units, as well as long-term storage. Other types of memory may include biological memory.

Memory 104 may store program instructions and/or data on which program instructions may operate. By way of example, memory 104 may store these program instructions on a non-transitory, computer-readable medium, such that the instructions are executable by processor 102 to carry out any of the methods, processes, or operations disclosed in this specification or the accompanying drawings.

As shown in FIG. 1, memory 104 may include firmware 104A, kernel 104B, and/or applications 104C. Firmware 104A may be program code used to boot or otherwise initiate some or all of computing device 100. Kernel 104B may be an operating system, including modules for memory management, scheduling and management of processes, input/output, and communication. Kernel 104B may also include device drivers that allow the operating system to communicate with the hardware modules (e.g., memory units, networking interfaces, ports, and busses), of computing device 100. Applications 104C may be one or more userspace software programs, such as web browsers or email clients, as well as any software libraries used by these programs. Memory 104 may also store data used by these and other programs and applications.

Network interface 106 may take the form of one or more wireline interfaces, such as Ethernet (e.g., Fast Ethernet, Gigabit Ethernet, and so on). Network interface 106 may also support communication over one or more non-Ethernet media, such as coaxial cables or power lines, or over wide-area media, such as Synchronous Optical Networking (SONET) or digital subscriber line (DSL) technologies. Network interface 106 may additionally take the form of one or more wireless interfaces, such as IEEE 802.11 (Wifi), BLUETOOTH®, global positioning system (GPS), or a wide-area wireless interface. However, other forms of physical layer interfaces and other types of standard or proprietary communication protocols may be used over network interface 106. Furthermore, network interface 106 may comprise multiple physical interfaces. For instance, some embodiments of computing device 100 may include Ethernet, BLUETOOTH®, and Wifi interfaces.

Input/output unit 108 may facilitate user and peripheral device interaction with example computing device 100. Input/output unit 108 may include one or more types of input devices, such as a keyboard, a mouse, a touch screen, and so on. Similarly, input I output unit 108 may include one or more types of output devices, such as a screen, monitor, printer, and/or one or more light emitting diodes (LEDs). Additionally or alternatively, computing device 100 may communicate with other devices using a universal serial bus (USB) or high-definition multimedia interface (HDMI) port interface, for example.

In some embodiments, one or more computing devices may be deployed in a networked architecture. The exact physical location, connectivity, and configuration of the computing devices may be unknown and/or unimportant to client devices. Accordingly, the computing devices may be referred to as "cloud-based" devices that may be housed at various remote locations.

Figure 2:
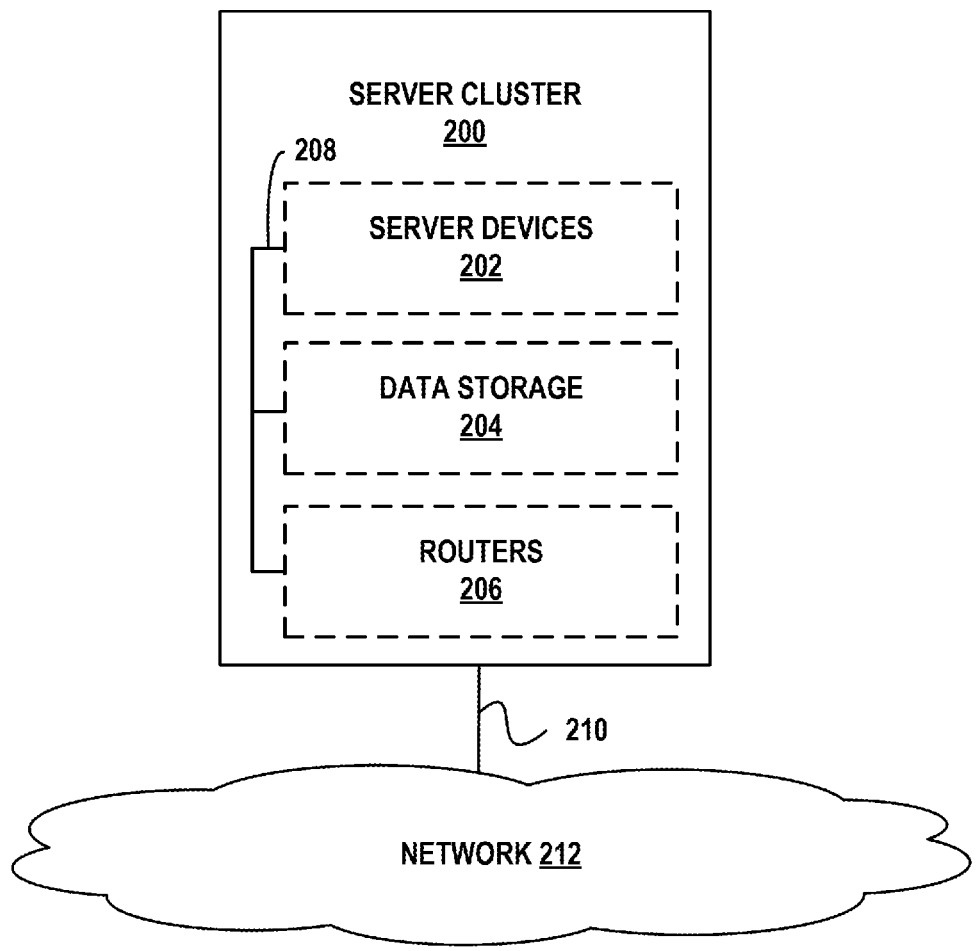
FIG. 2 illustrates a schematic drawing of a server device cluster, in accordance with example embodiments.

FIG. 2 depicts a cloud-based server cluster 200 in accordance with example embodiments. In FIG. 2, operations of a computing device (e.g., computing device 100) may be distributed between server devices 202, data storage 204, and routers 206, all of which may be connected by local cluster network 208. The number of server devices 202, data storages 204, and routers 206 in server cluster 200 may depend on the computing task(s) and/or applications assigned to server cluster 200.

For example, server devices 202 can be configured to perform various computing tasks of computing device 100. Thus, computing tasks can be distributed among one or more of server devices 202. To the extent that these computing tasks can be performed in parallel, such a distribution of tasks may reduce the total time to complete these tasks and return a result. For purpose of simplicity, both server cluster 200 and individual server devices 202 may be referred to as a "server device." This nomenclature should be understood to imply that one or more distinct server devices, data storage devices, and cluster routers may be involved in server device operations.

Data storage 204 may be data storage arrays that include drive array controllers configured to manage read and write access to groups of hard disk drives and/or solid state drives. The drive array controllers, alone or in conjunction with server devices 202, may also be configured to manage backup or redundant copies of the data stored in data storage 204 to protect against drive failures or other types of failures that prevent one or more of server devices 202 from accessing units of cluster data storage 204. Other types of memory aside from drives may be used.

Routers 206 may include networking equipment configured to provide internal and external communications for server cluster 200. For example, routers 206 may include one or more packet-switching and/or routing devices (including switches and/or gateways) configured to provide (i) network communications between server devices 202 and data storage 204 via cluster network 208, and/or (ii) network communications between the server cluster 200 and other devices via communication link 210 to network 212.

Additionally, the configuration of cluster routers 206 can be based at least in part on the data communication requirements of server devices 202 and data storage 204, the latency and throughput of the local cluster network 208, the latency, throughput, and cost of communication link 210, and/or other factors that may contribute to the cost, speed, fault-tolerance, resiliency, efficiency and/or other design goals of the system architecture.

As a possible example, data storage 204 may include any form of database, such as a structured query language (SQL) database. Various types of data structures may store the information in such a database, including but not limited to tables, arrays, lists, trees, and tuples. Furthermore, any databases in data storage 204 may be monolithic or distributed across multiple physical devices.

Server devices 202 may be configured to transmit data to and receive data from cluster data storage 204. This transmission and retrieval may take the form of SQL queries or other types of database queries, and the output of such queries, respectively. Additional text, images, video, and/or audio may be included as well. Furthermore, server devices 202 may organize the received data into web page representations. Such a representation may take the form of a markup language, such as the hypertext markup language (HTML), the extensible markup language (XML), or some other standardized or proprietary format. Moreover, server devices 202 may have the capability of executing various types of computerized scripting languages, such as but not limited to Perl, Python, PHP Hypertext Preprocessor (PHP), Active Server Pages (ASP), JavaScript, and so on. Computer program code written in these languages may facilitate the providing of web pages to client devices, as well as client device interaction with the web pages.

III. EXAMPLE DNA INFORMATION SYSTEM ARCHITECTURE

Figure 3:
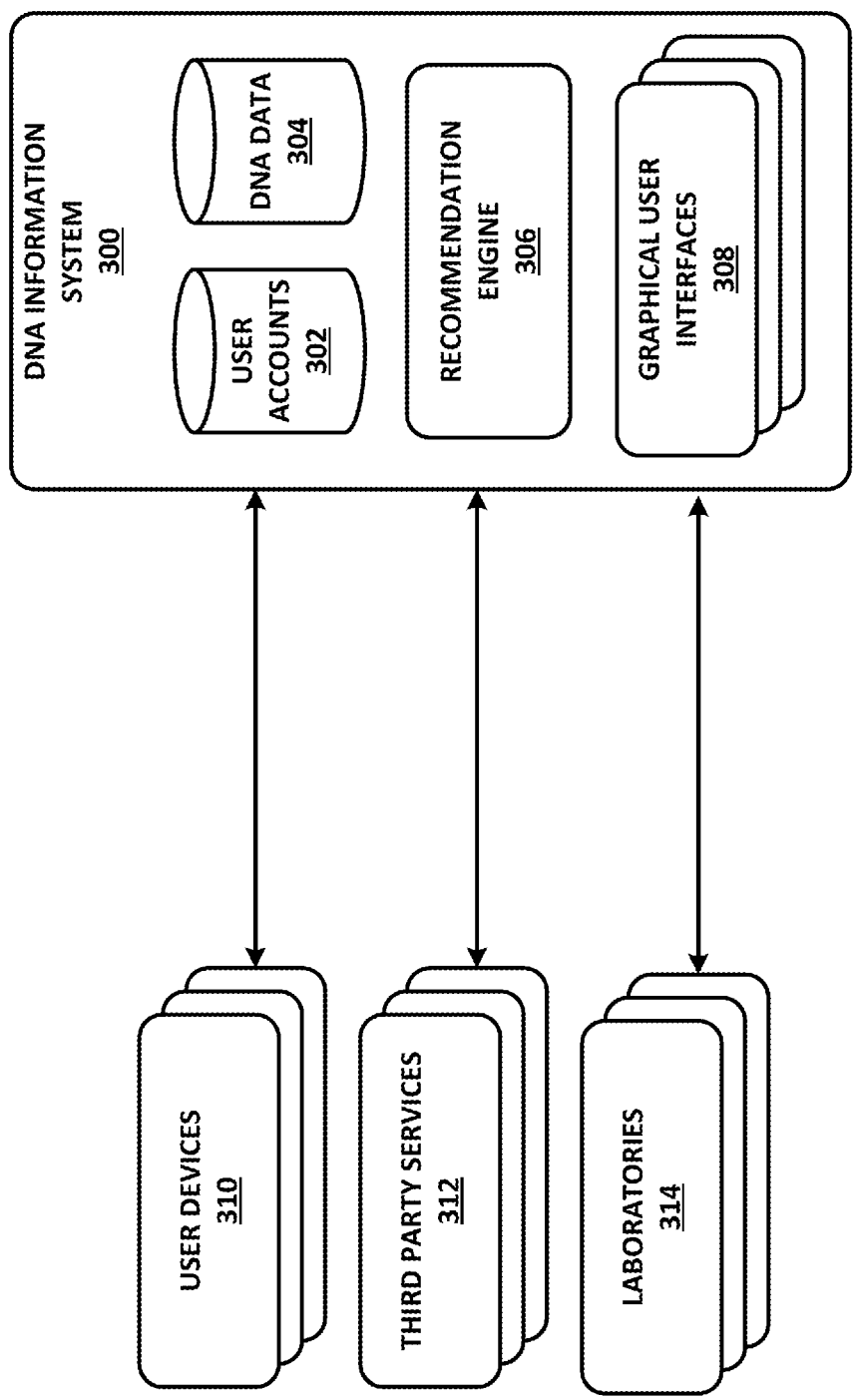
FIG. 3 depicts a DNA information system architecture, in accordance with example embodiments.

FIG. 3 depicts a DNA information system architecture, in accordance with example embodiments. This architecture includes four main components, DNA information system 300, user devices 310, third-party services 312, and laboratories 314. These components may all be connected via the Internet.

DNA information system 300, may be, for example, a DNA information provider network used by a business for receiving DNA information, parsing the DNA information, recommending cannabinoid formulations, and displaying certain aspects of the DNA information to a user. Thus, DNA information system 300 may include various user accounts 302, DNA data 304, a recommendation engine 306, and a plurality of graphical user interfaces 308.

User accounts 302 may be accounts that allow users to send DNA data 304 to DNA information system 300 and view details regarding DNA data 304 as well as recommendations for cannabinoid formulations via graphical user interfaces 308.

DNA data 304 may include raw DNA data provided by a user, or DNA data provided by laboratories 314. DNA data 304 may be transmitted over the Internet in the form of a plain text file. DNA data 304 may include large files, which can be cumbersome on DNA information system 300 because more network and storage resources are needed. One benefit of the embodiments disclosed herein is DNA information system 300 may be configured to parse DNA data 304 to extract only the DNA data relevant to a user's interactions with cannabinoid formulations. This allows DNA information system 300 to discard any irrelevant DNA data 304, freeing up network resources. Another benefit of parsing DNA data 304 and discarding irrelevant data is it maintains an extra level of privacy for the user. For example, if the security of DNA information system 300 was compromised, only the user's DNA data 304 associated with reactions to cannabinoids would be vulnerable, instead of the user's entire genome.

Recommendation engine 306 may be a component of DNA information system 300 configured to analyze DNA data 304 of a user and then provide a recommendation for cannabinoid formulations best suited for the user's DNA data 304. The recommendation may be based on a matching algorithm developed to pair cannabinoid formulations based on various SNPs found in a user's DNA data 304. For example, if a user is determined to have homozygous alleles (T/T) at the rs1045642 polymorphism for the ABCB1 gene, the user may be matched with a cannabinoid formulation that targets overall wellness because the user may have a lower risk of *cannabis* dependence relative to people with other genotypes. Recommendation engine 306 may be configured to provide a cannabinoid formulation recommendation for every user genotype in relation to the polymorphism for every gene associated with reactions to *cannabis*. Along with these recommendations, recommendation engine 306 may be configured to provide a user with a personalized endocannabinoid genotype report. The endocannabinoid genotype report may contain information regarding the different SNPs and their corresponding mental and/or physical health and wellness traits. This information may be particularly useful to a user because the information informs the user about the various effects cannabinoids may have on the user under certain circumstances. Recommendation engine 306 may also be configured to transmit the recommendations to a user via graphical user interfaces 308.

Graphical user interfaces 308 may include one or more web-based graphical user interfaces configured to display DNA data 304 and the recommendation provided by recommendation engine 306.

User devices 310 may include a plurality of computing devices 100, as described in FIG. 1. User devices 310 may be configured to carry out a plurality of actions, including but not limited to (i) setting up a user account 302 at DNA information system 300, (ii) transmitting DNA data 304 to DNA information system 300, (iii) viewing recommendations and other DNA information via graphical user interfaces 308. For example, a user may connect to DNA information system 300 on a user device 310 (e.g., a smartphone) via the Internet. The user may create a user account 102, registering with DNA information system 300. The user may then transmit DNA data 304 in the form of a plain text file. The user may, when ready, view the recommendation from recommendation engine 106 on user device 310 via graphical user interfaces 308.

Third-party services 312 may include, for example, various DNA information providers, such as 23ANDME® and ANCESTRY.COM®. These third-party services 312 may offer a variety of services, including sending DNA test kits to users. These DNA test kits may include elements configured to receive DNA samples from users (e.g., test tubes for saliva deposits). Once a user completes a DNA test kit and returns it to a third-party service 312, the third-party service 312 may send the DNA samples to laboratories 314.

Laboratories 314 may be laboratories that, for example, receive DNA samples and analyze the samples to create raw DNA data. This raw DNA data may include some or all of a user's genome in the form of a text file. Laboratories 314 may be partnered with DNA information system 300 or third-party services 312 to provide DNA data 304. Laboratories 314 may configure DNA data 304 to be parsed and analyzed by recommendation engine 306 of DNA information system 300.

After DNA data 304 is parsed and analyzed by DNA information system 300, DNA information may provide a personalized endocannabinoid genotype report to the user. The endocannabinoid report may contain detailed information related to different endocannabinoid genotype markers.

IV. EXAMPLE ENDOCANNABINOID GENOTYPE MARKERS

It is desirable for a user to fully understand and comprehend the different mental and physical traits that may be affected when using certain cannabinoid compounds. For instance, DNA data 304 may indicate that a user has a greater risk for anxiety in a stressful situation relative to other genotypes. This indication is determined by analyzing the user's genotype at a particular polymorphism for a particular gene. For example, with respect to a user's propensity for anxiety, DNA information system 300 analyzes the user's genotype at (i) the polymorphism rs1049353 for the CNR1 gene, (ii) the polymorphism rs324420 at the FAAH gene, and (iii) the 5-HTTLPR polymorphism for the SLC6A4 gene.

Along with anxiety, there are a number of traits that may be affected by cannabinoid usage. Each of these traits has an associated polymorphism for different genes. For purposes of this disclosure, the terms "SNP" and "polymorphism" may be used interchangeably.

A. Anxiety

Anxiety is a common disorder experienced by many individuals. While the study behind the causes and effects of anxiety are ever changing, there have been several SNPs discovered that relate to the interaction of anxiety and cannabinoids. For example, the SNP rs1049353 for the CNR1 gene is associated with activation of specific brain areas (the insula and amygdala). The effect of this related to how one gauges visual, emotional, and social cues. Examples include facial expressions that change from anger to sadness or fear; happiness to sadness or fear; and neutral. Another example is the SNP rs324420 for the FAAH gene, which is associated with how an individual's endocannabinoid system (ECS) is related to specific neural mechanisms which may impact complex behavioral processes related to risk for addiction, dependence, and obesity. Yet another example is the SNP 5-HTTLPR for the SLC6A4 gene, which is associated with the development of anxiety for youth users of *cannabis*. By analyzing these SNPs, DNA information system 300 may be able to effectively recommend certain cannabinoid formulations tailored to a user's DNA.

B. Bipolar Disorder

Bipolar disorder, or manic depression, is a serious brain illness that causes unusual shifts in mood, energy, activity, and the ability to carry out daily activities. Individuals suffering from bipolar disorder experience periods of intense emotion, changes in sleep, and unusual behavior, known as episodes. Episodes can be categorized as either manic (more energetic and "up" than normal) or depressive (more low energy and "down" than normal). While research surrounding bipolar disorder is ever changing, researchers have identified a SNP associated with the risk for developing bipolar disorder. For example, the SNP rs41311993 for the CNR2 gene is associated with the risk for developing bipolar disorder. Using this association, DNA information system 300 can recommend a cannabinoid formulation that will react positively with a user that has a lower/higher risk of developing bipolar disorder.

C. Cognitive Function

Cognitive function may, for example, relate to a user's ability of their brain to process information and knowledge. While this is a general trait, researchers have identified SNPs that indicate how *cannabis* may affect a user's cognitive function. In one example, the SNP rs1049353 for the CNR1 gene is associated with lower performance of executive function and sustained attention. Thus, depending on their endocannabinoid genotype, some users may experience an elevated risk of not being able to sustain attention when using *cannabis*. In another example, the SNP rs4680 for the COMT gene is associated with risk of structural brain changes following *cannabis* use. Users that have an at-risk genotype for this SNP (e.g., homozygous alleles, such as (A/A)), may want to consult with a specialist in cognitive function before using *cannabis*. In yet another example, the SNP rs12199634 for the MAPK14 gene is associated with a risk of decreased white matter brain volume from *cannabis* use, which may result in impairing a user's cognitive function. In another example, the SNP rs7834206 for the NRG1 gene is associated with auditory reception when using *cannabis*. Users with heterozygous alleles (C/A) may be more likely to have auditory discrepancies after using *cannabis* when compared to users with other genotypes. In yet another example, the SNP 5-HTTLPR for the SLC6A4 gene is associated with a user's focus, visual interpretation of their environment, and decision making. Users with homozygous alleles (L'/L') might not experience a decrease in brain performance when using *cannabis*.

D. Depression

Depression may, for example, relate to how a user feels, thinks, and acts. Specifically, depression is a long-term mental degradation that can affect the way a user functions in daily life. Depression can further be characterized by feeling tearful, irritable, and having diminished interest or pleasure in activities every day; significant weight loss/decrease or increase in appetite; inability to get to sleep or difficulty staying asleep or sleeping too much; problems with sitting or a slowing of one's movements; talking very quietly with slowed speech; fatigue; tiredness; feelings of worthlessness; diminished ability to think or concentrate; recurrent thoughts of death (not just fear of dying); recurrent suicidal ideas without a specific plan; or a suicide attempt or creating a specific plan for committing suicide. Due to the severity of depression symptoms, it is beneficial to have an understanding of how *cannabis* may affect users that have a particular genotype. For example, the SNP rs1049353 for the CNR1 gene is associated with depression—specifically, how a user reacts to certain antidepressants such as citalopram. Users that have heterozygous alleles (C/T) may have a decrease likelihood of responding to antidepressants. In another example, the SNP rs2023239 for the CNR1 gene is associated with depression generally. Users that have homozygous alleles (T/T) may experience a higher likelihood of exacerbating pre-existing symptoms of depression when using *cannabis*. In yet another example, the SNP rs806377 for the CNR1 gene is associated with how a user responds to positive emotional stimuli. Users with homozygous alleles (T/T) may experience a higher amount of positive emotions after a positive event than people with heterozygous alleles. In yet another example, the SNP rs324420 for the FAAH gene is associated with white matter integrity in the brain and increased reports of depression and apathy in *cannabis* users. Users with homozygous alleles (CC) may experience decreased white matter in the brain and weakened brain structure when *cannabis* is used at a young age. This information may be particularly useful when determining which cannabinoid formulation to recommend to a user.

E. Impulsive Behavior

Impulsive behavior may, for example, relate to making decisions without thinking of the results and/or consequences beforehand. Impulsive behavior has many causes, which can include mental disorders such as hyperactivity disorder or personality disorders, such as borderline personality disorder. *Cannabis* usage may also cause impulsivity for certain users. For example, the SNP rs1049353 for the CNR1 gene is associated with adolescent psychosocial adversity, which is how one responds and/or adapts to family or relationship problems, health problems, school and other structural worries, and how they relate to impulsive behavior. Users with a genotype containing heterozygous alleles (C/T) may have an elevated risk of impulsive behavior when using *cannabis*. In another example, the SNP rs806379 for the CNR1 gene is also associated with adolescent psychosocial adversity. Users with homozygous alleles (A/A) that experienced early psychosocial adversity may have a higher risk of impulsive behavior. In yet another example, the SNP rs1611115 for the DBH gene is associated with impulsivity after *cannabis* consumption. Users with homozygous alleles (C/C) might not have increased impulsivity after *cannabis* use, while users with heterozygous alleles may have increased impulsivity after *cannabis* use. In yet another example, the SNP rs221533 for the NRG1 gene is associated with lower inhibition and significantly riskier decision making. Users with heterozygous alleles (T/C) may have a lower risk of having behaviors associated with risky decision making when using *cannabis*. In yet another example, the SNP rs28363170 for the SLC6A3 gene is also associated with impulsivity when using *cannabis*. Users with homozygous alleles (10R/10R) may have a lower risk of impulsivity after consuming *cannabis* compared to users with heterozygous alleles.

F. Memory Impairment

Memory impairment may, for example, relate to a person's ability to store information in their brain. For example, the SNP rs1049353 for the CNR1 gene is associated with varying brain awareness states, which is related to working memory ability and other cognitive functions. Users with heterozygous alleles (CT) may have a normal state of awareness when compared to users with a different genotype. In another example, the SNP rs1406977 for the CNR1 gene is associated with performance on working memory tasks when using *cannabis*. Users with homozygous alleles (T/T) may be less likely to experience working memory impairments after use of THC.

G. Metabolic Function

Metabolic function may, for example, relate to how a user's cells breaks down materials from food to energy. Metabolic function may vary in users that are consuming *cannabis*. For example, the SNP rs1045642 for the ABCB1 gene is associated with THC levels and THC metabolites in *cannabis* users. Users with homozygous alleles (T/T) may have two-fold lower blood THC levels after consuming THC relative to people with a different genotype. In another example, the SNP rs1057910 for the CYP2C9 gene is associated with how oral THC is processed or metabolized in the body. Users with homozygous alleles (A/A) are typically no more sensitive to oral THC.

H. Migraines

Migraines may, for example, relate to severe headaches that occur on one side of the head. Migraines can cause extreme discomfort and symptoms such as nausea and oversensitivity to lights and sounds. Research indicates that *cannabis* usage may have an effect on migraines in certain individuals. For example, the SNP rs806366 for the CNR1 gene is associated with a user's susceptibility to migraines. Users with homozygous alleles (T/T) may be more likely to develop migraines after stressful events. This is beneficial information because a medical provider can prescribe an appropriate dose if the provider is aware that the user is more likely to develop migraines.

I. Motor Control

Motor control may, for example, relate to the process of creating and sending purposeful, voluntary movements throughout the body. Research indicates that the consumption of *cannabis* may have profound effects on a user's motor control. For example, the SNP rs1130233 for the AKT1 gene is associated with the degree of impairment in a user's psychomotor control and/or motor coordination after consumption of THC. Users with heterozygous alleles (C/T) may develop impaired motor coordination and slowed down thinking after consuming THC.

J. Opioid Effects

Opioids are, for example, a class of drugs created from the opium poppy plant. The plants are harvested and used in various types of medications because they contain a chemical that relaxes the body, and helps to relieve pain. Examples of opioids include Hydrocodone, Oxycodone, Oxymorphone, Morphine, Fentanyl, and Codeine. Research indicates that particular genetic markers may affect how a user reacts to opioids. For example, the SNP rs324420 for the FAAH gene is associated with having adverse opioid effects when combined with how a user's endocannabinoid system modulates, by way of such cannabinoids such as anandamide. Users with homozygous alleles (C/C) may have a lower risk of experienced side effects from opioids relative to people with a different genotype.

K. Pain

Pain may, for example, relate to the unpleasant and corresponding emotional reaction in response to injury or tissue damage. Pain is a signal sent through the spinal cord, to a user's brain, alerting her that something is wrong in her body. Pain can be difficult to diagnose as it can manifest itself in different ways for different people. For example, the SNP rs324420 for the FAAH gene is associated with pain sensitivity and use of postoperative analgesia. Users with homozygous alleles (C/C) may have higher pain sensitivity to cold temperatures and more need for analgesia during periods of acute pain, such as after an operation. This information is beneficial when a provider is prescribing cannabis after an operation.

L. Psychosis

Psychosis may, for example, relate to a user's propensity for becoming disconnected from reality. Psychosis from cannabis can cause delusions, which are strong beliefs that don't make sense and/or are not consistent with the user's actual beliefs. Research indicates that cannabis may have a more profound effect on users with particular genetic markers. For example, the SNP rs1130233 for the AKT1 gene is associated with the risk of psychosis-like effects (e.g., include delusion, delirium and confusion) after consuming THC. Users with heterozygous alleles (C/T) may have an increased risk of experience acute psychosis-like effects after consuming THC. In another example, the SNP rs2494732 for the AKT1 gene is associated with the risk of psychotic episode in users that consume cannabis. Users with homozygous alleles (T/T) may have a lower risk of experiencing psychotic disorder effects after consuming THC. In yet another example, the SNP rs6265 for the BDNF gene is associated with the onset of a psychotic disorder at a young age. Users with homozygous alleles (G/G) may not be at risk for onset psychosis if the user is already predisposed to developing psychosis.

In yet another example, the SNP rs4680 for the COMT gene is also associated with psychosis-like effects (e.g., delusion, delirium, and confusion) after consuming THC. Users with homozygous alleles (A/A) may be less likely to experience psychosis-like effects after consuming THC relative to people with different genotypes. In another example, the SNP rs1076560 for the DRD2 gene is associated with a greater risk of developing psychosis (e.g., having regular hallucinations and delusions) in cannabis users. In yet another example, the SNP rs2494732 for the AKT1 gene is associated with a risk of a psychotic disorder and cognitive disabilities, including verbal memory and sustained attention impairments. Users with homozygous alleles (T/T) may have a lower risk of psychotic disorder and a lower risk of memory and attention impairments after consuming THC than users with a different genotype. This information may be particularly beneficial as it may prevent a user that is predisposed to psychosis from overdosing on THC.

M. Psychotic Like Effects

Psychotic like effects may, for example, include delusions and delirium caused by cannabis usage. Research indicates that cannabis use can cause schizophrenia, an illness that can cause a person to feel as if they have lost touch with reality. Research also indicates that certain genetic markers can indicate whether an individual is more likely to experience psychotic like effects when consuming cannabis. For example, the SNP 5-HTTLPR for the gene SLC6A4 is associated with psychotic like effects in user with bipolar disorder when that user consumes cannabis.

N. Sleep Quality

Sleep quality may, for example, relate to the amount of time a user sleeps, the amount of times a user wakes up during the night, and the amount of time it takes a user to fall asleep. Research indicates certain genetic markers are related to sleep quality. For example, the SNP rs324420 for the FAAH gene is associated with poorer sleep quality among young cannabis users who exhibit depression symptoms. Users with homozygous alleles (C/C) may have an increased risk of poor sleep quality while using certain cannabinoid formulations.

V. EXAMPLE GRAPHICAL USER INTERFACES

The embodiments described herein are directed as presenting DNA data 304's associated traits and conditions to a user via a plurality of graphical user interfaces. Presenting the information in this way may allow users to choose the most effective cannabis strains and compounds while avoiding cannabis compounds that might have negative impacts based on their endocannabinoid genotype.

FIGS. 4A-4H depict graphical user interfaces showing DNA information at a DNA information provider view, in accordance with example embodiments. Each of these graphical user interfaces may be provided for display on a client device. The information provided therein may be derived, at least in part, from DNA data 304 stored in a database that is part of DNA information system 300. Nonetheless, these graphical user interfaces are merely for purpose of illustration. The applications described herein may provide a graphical user interface that formats information differently, includes more or less information, and includes different types of information.

One of the difficulties DNA information providers encounter is that it is challenging to be able to receive raw DNA data and be able to subsequently display that information to a user in a way that is easily understandable. Another difficulty is being able to recommend particular cannabinoid compounds based on a user's endocannabinoid genotype. As discussed above, every individual has an endocannabinoid system comprised of chemical receptors in the brain, immune system, and central nervous system (for example, cannabinoid receptors CB1 and CB2).

As described above, DNA data (such as DNA data 304) may be collected from users directly, or third-party services that previously sent a user a DNA testing kit. For a DNA information provider, collecting and storing all of this data may be taxing on hardware and network resources. As a consequence, technical tools are required to be able to parse and process the DNA data so that it can be presented in a manageable fashion on one or more configurable graphical user interfaces.

Notably, the embodiments herein require computer implementation. By its very nature, receiving and parsing DNA information is premised on the existence of computers and computer networks. The human genome consists of over three billion base pairs, which would take a human an unrealistic amount of time to parse to locate the specific polymorphisms discussed herein.

Non-limiting examples of such graphical user interfaces are described below. Nonetheless, these examples are made for purpose of illustration, and other graphical user interfaces, and layouts of information therein, may be possible.

Figure 4A:
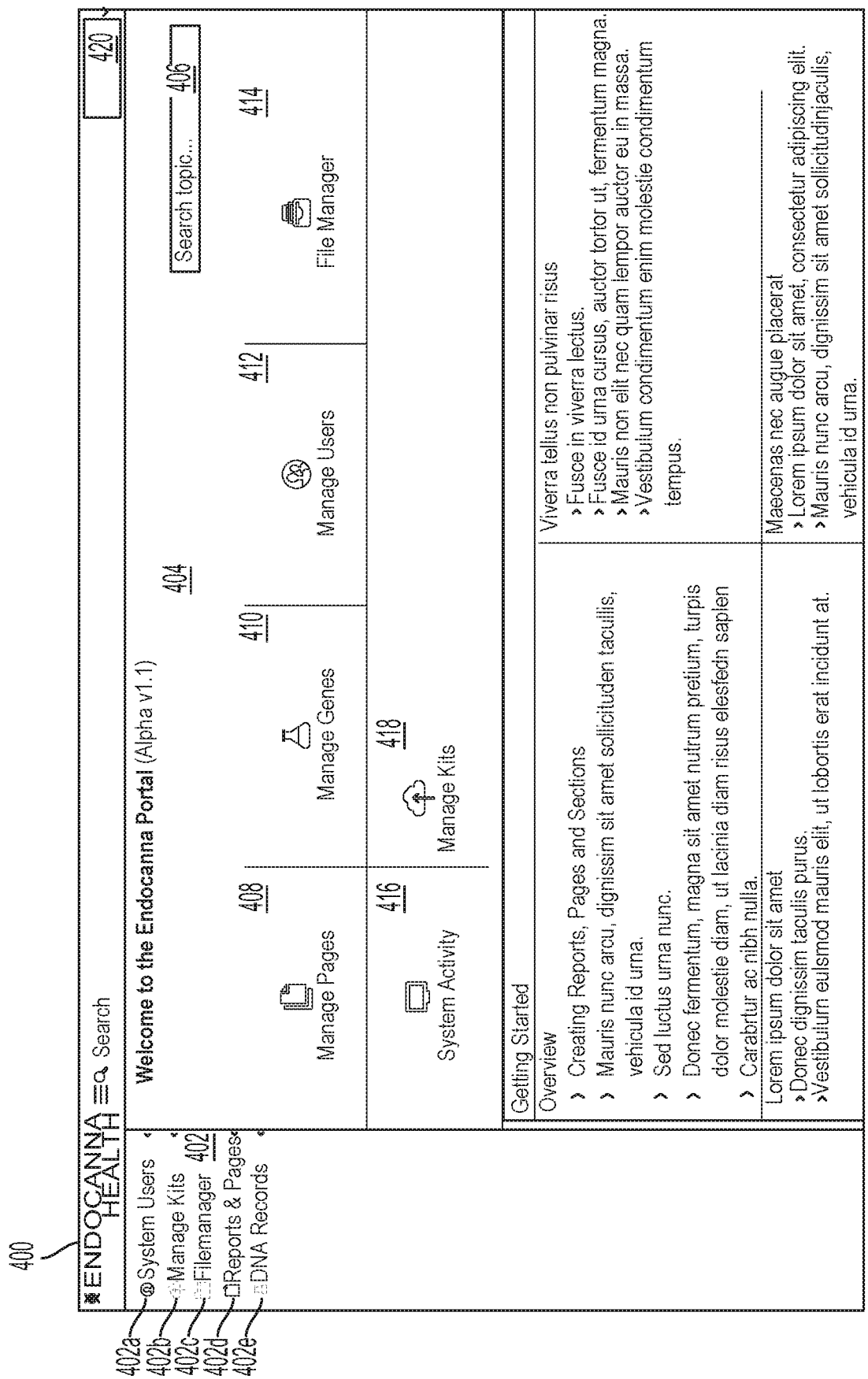
FIG. 4A depicts a graphical user interface showing DNA information at a DNA information provider view, in accordance with example embodiments.

FIG. 4A depicts a graphical user interface 400 at a DNA information provider view. The view of a DNA information provider may include the view of a network administrator. Graphical user interface 400 includes a navigation pane 402, page view 404, search bar 406, navigation tiles 408, 410, 412, 414, 416 and 418, and user information 420.

Navigation pane 402 includes a plurality of selectable buttons that are configured to navigate to different instances of graphical user interface 400. For example, navigation pane 402 includes a button for system users 402a, manage kits 402b, file manager 402c, reports and pages 402d, and DNA records 402e.

Page view 404 corresponds to the button selected in navigation pane 402. For example, page view 404 changes if file manager 402c is selected. As shown in FIG. 4A, page view 404 displays a welcome message, along with selectable navigation tiles 408, 410, 412, 414, 416, and 418.

Navigation tiles 408, 410, 412, 414, 416, and 418 may provide a user with shortcuts to various types of information deemed important. For example, selecting navigation tile 408 takes a user to the manage pages section of reports and pages 402d. By selecting navigation tile 408, the user can more efficiently reach the desired section, instead of having to select reports and pages 402d and then select the manage pages option. In another example, selecting navigation tile 410 takes a user to the manage genes section of DNA records 402e. Similarly, selecting navigation tiles 412 and 414 take a user to the manage users section of system users 402a and file manager 402c, respectively. Selecting navigation tile 416 may bring a user to a system activity page that displays user account activity (e.g., a user id, a username, a code, an activity message, and a time stamp). This information may be beneficial when compiling data on user traffic. Selecting navigation tile 418 may have similar functionality to selecting manage kits 402b.

User information 420 may include the account information for the user that is logged in. For example, selecting user information 420 may provide options to view a profile associated with the user and/or a selectable button to log out of the current user account.

In operation, selecting one of the selectable buttons in navigation pane 402, or one of the navigation tiles 408, 410, 412, 414, 416, or 418, will cause graphical user interface 400 to change and display different information. For example, system users 402a may be selectable and once selected, may display selectable options for "manage users" and "manage permissions" (not shown). Selecting "manage users" may cause graphical user interface 400 to display information related to user accounts that are registered with DNA information system 300.

FIG. 4B, similarly to FIG. 4A, depicts a graphical user interface 400 at a DNA information provider view. In FIG. 4B, graphical user interface 400 includes a system users table 422, table header row 424, table rows 424a, 424b, 424c, 424d, 424e, 424f, 424g, 424h, 424i, and 424j, table manipulator button 426, and table navigation button 428.

System users table 422 includes entries for each user that has created a user account with DNA information system 300. Each user account is stored in user accounts 302, as shown in FIG. 3. Table header row 424 displays the different types of information contained in the table. As shown in FIG. 4B, the system users table 422 includes fields for "Last Name," "First Name." "Email (login)," "Permissions," and "Action." The "Last Name" and "First Name" fields correspond to a user's given last and first names, respectively. The "Email (login)" field corresponds to the user's email address (which is provided by the user during the account creation process). The "Permissions" field corresponds to the user's permission group. As shown in FIG. 4B, the two available permissions are "member" or "admin." These permissions may be created and/or modified by an administrator associated with a DNA information provider via graphical user interface 400 (not shown). The "Action" field may include selectable buttons that allow an administrator to edit a user's information, or delete a user altogether.

Table rows 424a, 424b, 424c, 424d, 424e, 424f, 424g. 424h. 424i, and 424j include information relating to the information fields in table header row 424. For example, table row 424c has "Hayes" for the "Last Name" field, "Ricky" for the "First Name" field, "user3@gmail.com" for the "Email" field, "member" for the "Permissions" field, and "Edit/Delete" for the "Action" field.

In operation, if an administrator wanted to remove Phillip Fry from user accounts 302, the administrator would select the "Delete" button in the "Action" column of table row 424g. Similarly, if an administrator wanted to edit the first name, last name, or email address of Jason Taylor, the administrator could select the "Edit" button in the "Action" column of table row 424j.

Table manipulator button 426 includes a selectable button to add an entry to system users table 422. Once selected, a window may be displayed allowing the administrator to manually enter user information to create an account (not shown). Table navigation button 428 is a series of selectable buttons allowing an administrator to view additional user accounts and information.

Turning back to FIG. 4A, after a user is satisfied with viewing user accounts 302 via system users table 422, the administrator may select manage kits 402b via navigation pane 402. While the user may select manage kits 402b, the user can select any button in navigation pane 402.

FIG. 4C, similarly to FIG. 4A, depicts a graphical user interface 400 at a DNA information provider view. In FIG. 4C, graphical user interface 400 includes a system registered kits table 430, table header row 432, table rows 432a, 432b, 432c, 432d, 432e. 432f, 432g, 432h, 432i, and 432j, table manipulator button 434, and table navigation button 436.

Registered kits table 430 includes entries for each user that has received a DNA testing kit from DNA information system 300. Each kit is stored in DNA data 304, as shown in FIG. 3. Table header row 432 displays the different types of information contained in the table. As shown in FIG. 4C, the registered kits table 430 includes fields for "Name," "Email," "Phone," "Barcode," "Status," "Created On," and "Action." The "Name" field corresponds to a user's given name (or the name entered by the user during account creation). The "Email" field corresponds to the user's email address, which is provided by the user during the account creation process. The "Phone" field corresponds to the phone number entered during account creation. The "Barcode" field corresponds to the barcode printed on the DNA testing kit that was sent to the user. The "Status" field corresponds to the whether the user has registered the DNA kit—the two statuses for purposes of this field are "registered" and "unregistered." The "Created On" field corresponds to the date and time the user registered the kit. The "Action" field includes a selectable button that allows an administrator to upload the results of the completed DNA kit for viewing by the user.

Table rows table rows 432a, 432b, 432c, 432d, 432e, 432f, 432g, 432h, 432i, and 432j include information relating to the information fields in table header row 432. For example, table row 434f has "Simpson, Katie" for the "Name" field, "user6@gmail.com" for the "Email" field, "(555) 186-7482" for the "Phone" field, "7513-784614" for the "Barcode" field, "registered" for the "Status" field, "20188-14 08:03 AM" for the "Created On" field, and "Upload Results" for the "Action" field.

Table manipulator button 434 includes a selectable button to add an entry to registered kits table 430. Once selected, a window may be displayed allowing the administrator to manually enter user information to create a registered kit (not shown). Table navigation button 436 is a series of selectable buttons allowing an administrator to view additional registered kits and related information.

Turning back to FIG. 4A, after a user is satisfied with viewing and editing registered kits via system users table 430, the administrator may select file manager 402c via navigation pane 402. While the user may select file manager 402c, the user can select any button in navigation pane 402.

Figure 4D:
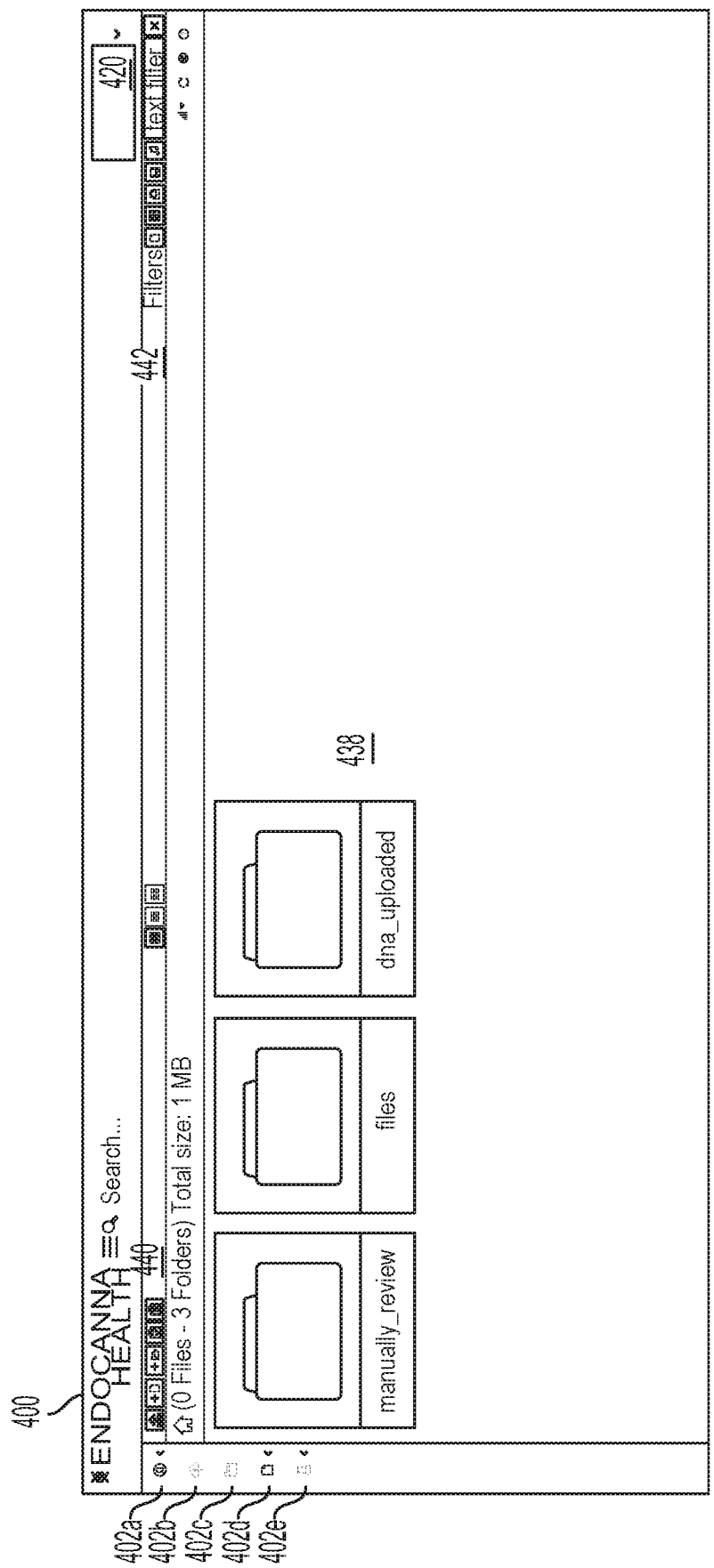
FIG. 4D depicts a graphical user interface also showing DNA information at the DNA information provider view, in accordance with example embodiments.

FIG. 4D depicts a graphical user interface 400 at a DNA information provider view. In FIG. 4D, graphical user interface 400 includes file folders 438, file manipulator buttons 440, and file filters 442.

File folders 438 are folders that contain various files related to DNA information system 300. For example, file folders 438 may include files to be manually reviewed, general files, and uploaded DNA files. Files to be manually reviewed may include test files that have been created and are in an approval phase. These files can include new images, formulation icons, or customized DNA files. General files may include images that appear on the end-user view of the graphical user interface, various icons, and notes. Uploaded DNA files may include raw DNA files that were transmitted to DNA information system 300 via user devices 310, third-party services 312, and/or laboratories 314. As discussed previously, the uploaded DNA files may have been parsed and reduced by DNA information system 300 to display the SNPs most relevant to a user's endocannabinoid system. This is beneficial as it reduces the amount of network resources required to store and display DNA data 304.

File manipulator buttons 440 are buttons configured to upload files, create new files, create new folders, paste a set of files and/or folders into the current directory, and clear the clipboard of any copied files and/or folders.

File filters 442 are buttons configured to filter the currently viewed files and folders by file type, images, archived files and/or folders, videos, music, and/or text. For example, if a user wanted to only view files and folders that contained images, he or she may select the images filter in file filters 442. In another example, if the user wanted to filter the files and/or folders by a particular text string, the user could enter the text string into the text filter window of file filters 442. In this example, inputting "sleep" into the text filter window of file filters 442 may result in file folders 438 displaying only files and folders that contain images related to sleeping.

After a user is satisfied with viewing and editing files and folders via file folders 438, the administrator may select manage reports under reports and pages 402d via navigation pane 402. While the user may select reports and pages 402d, the user can select any button in navigation pane 402.

FIG. 4E depicts a graphical user interface 400 at a DNA information provider view. In FIG. 4E, graphical user interface 400 includes reports table 444, table header row 446, table row 446a, and table manipulator button 448.

Reports table 444 includes entries for each report DNA information system 300 is providing to user devices 310. Each report contains DNA data 304 and the recommendation generated by recommendation engine 306. A separate report may be generated for each user and DNA data 304 may be filtered to include only DNA data 304 that is relevant to each user's endocannabinoid genotype. Reports table 444 also includes table header row 446 and table row 446a. Table header row 446 displays the different types of information contained in reports table 444 and table row 446a displays the information for a particular report. As shown in FIG. 4E, table header row 446 includes fields for "Slug," "Title," "Type," "Author," "Status," and "Action." The "Slug" field corresponds to the genetic profile for which the polymorphisms have an effect. For example, table row 446a in FIG. 4E displays the slug is "ecs," or endocannabinoid system. This indicates the polymorphisms in the report pertain to a user's endocannabinoid system. The "Title" field corresponds to the title of the report. As shown in table row 446a, the title of the report is "Endocannabinoid DNA." The "Type" field corresponds to the type of report. The "Author" field corresponds to the DNA information provider that created the report. The "Status" field corresponds to the whether the report has been published on the end-user view of graphical user interfaces 308 on DNA information system 300 the two statuses for purposes of this field are "published" and "unpublished." The "Action" field includes a selectable button that allows an administrator to edit the selected report.

Table manipulator button 448 has the same functionality as table manipulator button 426 in FIG. 4B and table manipulator button 434 in FIG. 4C. Specifically, table manipulator button 448 allows an administrator to add a report to reports table 444.

After a user is satisfied with viewing and editing reports via reports table 444, the administrator may select manage pages under reports and pages 402d via navigation pane 402. While the user may select manage pages under reports and pages 402d, the user can select any button in navigation pane 402.

FIG. 4F depicts a graphical user interface 400 at a DNA information provider view. In FIG. 4F, graphical user interface 400 includes pages table 450, table header row 452, table rows 452a, 452b, 452c, 452d. 452e, 452f. 452g, 452h, 452i, and 452j, table manipulator button 454, and table navigation button 456.

Pages table 450 includes entries for each page DNA information system 300 is providing to user devices 310. Each page contains information regarding the DNA information provider or information generated to educate an end-user about their DNA information. Table header row 452 displays the different types of information contained in pages table 450 and table rows 452a, 452b, 452c, 452d, 452e, 452f, 452g, 452h, 452i, and 452j display the information for a particular page. As shown in FIG. 4F, table header row 452 includes fields for "Parent," "Title," "Page Type," "Status," "Updated On," and "Action." The "Parent" field corresponds to the genotype report for which the page is related. For example, table row 452e in FIG. 4F indicates the parent report is ecs, or the Endocannabinoid DNA report from FIG. 4E. The "Title" field corresponds to the title of the page. As shown in table row 452d, the title of the page is "Welcome To Your Cannabinoid DNA Variant Report." The "Page Type" field corresponds to the type of page. The types of pages may include articles, detailed reports, report summaries, and general information. The "Status" field corresponds to the whether the report has been published on the end-user view of graphical user interfaces 308 on DNA information system 300—the two statuses for purposes of this field are "published" and "unpublished." The "Action"

field may include selectable buttons that allow an administrator to edit a page's information, or delete a page altogether.

Table rows 452a, 452b, 452c, 452d, 452e, 452f, 452g, 452h, 452i, and 452j include information relating to the information fields in table header row 452. For example, table row 452h has "none" for the "Parent" field, "DNA 101" for the "Title" field, "article" for the "Page Type" field, "published" for the "Status" field, "0804/2018" for the "Updated On" field, and "Edit or Delete" for the "Action" field.

Table manipulator button 454 has the same functionality as table manipulator button 426 in FIG. 4B, table manipulator button 434 in FIG. 4C, and table manipulator button 448 in FIG. 4E. Specifically, table manipulator button 454 allows an administrator to add a page to pages table 450. Table navigation button 456 has the same or similar functionality as table navigation button 428 in FIG. 4B and table navigation button 436 in FIG. 4C.

After a user is satisfied with viewing and editing pages via pages table 450, the administrator may select manage sections under reports and pages 402d via navigation pane 402. While the user may select manage sections under reports and pages 402d, the user can select any button in navigation pane 402.

FIG. 4G depicts a graphical user interface 400 at a DNA information provider view. In FIG. 4G, graphical user interface 400 includes sections table 458, table header row 460, table rows 460, 460b, 460c, 460d, 460e, 460f, 460g, 460h, 460i, and 460j, table manipulator button 462, and table navigation button 464.

Sections table 458 includes entries for each section DNA information system 300 is providing to user devices 310. Each section contains information regarding conditions that effect a user's endocannabinoid system or information generated to educate an end-user about how their particular DNA may interact with certain cannabinoid compounds. Table header row 460 displays the different types of information contained in sections table 458 and table rows table rows 460a, 460b, 460c, 460d, 460e, 460f, 460g, 460h, 460i, and 460j display the information for a particular section. As shown in FIG. 4G, table header row 460 includes fields for "Parent," "Slug," "Page Type," "Status," "Updated On," and "Action." The "Parent" field corresponds to the genotype report and page for which the section is related. For example, table row 460e in FIG. 4G indicates the parent page is "ecs-cognitive", or the "ECS Cognitive Function" page from FIG. 4F. The "slug" field corresponds to particular SNP the information corresponds to. As shown in table row 460d, the slug being referred to is "ecs_bipolar_rs41311993," which corresponds to information regarding how *cannabis* use may affect a user with a particular genotype at the SNP rs41411993. The "Page Type" field corresponds to the type of section. The types of pages for sections table 458 may include sections, detailed reports, report summaries, and general information. The "Status" field corresponds to the whether the report has been published on the end-user view of graphical user interfaces 308 on DNA information system 300—the two statuses for purposes of this field are "published" and "unpublished." The "Action" field may include selectable buttons that allow an administrator to edit a section's information, or delete a section altogether.

Table rows table rows 460a, 460b, 460c, 460d, 460e, 460f, 460g, 460h, 460i, and 460j include information relating to the information fields in table header row 460. For example, table row 460i has "ecs_cognitive" for the "Parent" field, "ecs_cognitive_rs7834206" for the "Slug" field, "section" for the "Page Type" field, "published" for the "Status" field, "NULL" for the "Updated On" field (indicating that the section has not been updated since creation), and "Edit or Delete" for the "Action" field.

Table manipulator button 462 has the same functionality as table manipulator button 426 in FIG. 4B, table manipulator button 434 in FIG. 4C, and table manipulator button 448 in FIG. 4E. Specifically, table manipulator button 462 allows an administrator to add a section to sections table 458. Table navigation button 464 has the same or similar functionality as table navigation button 428 in FIG. 4B and table navigation button 436 in FIG. 4C.

After a user is satisfied with viewing and editing sections via sections table 458, the administrator may select manage user DNA under DNA records 402e via navigation pane 402. While the user may select manage user DNA under DNA records 402e, the user can select any button in navigation pane 402.

FIG. 4H depicts a graphical user interface 400 at a DNA information provider view. In FIG. 4H, graphical user interface 400 includes user raw data 466, table header row 468, table rows 468a, 468b, 468c, 468d, 468e, 468f, 468g, 468h, 468i, and 468j, table manipulator button 470, and table navigation button 472.

User raw data table 466 includes entries for the raw DNA data for each user that has uploaded DNA data 304 to DNA information system 300. Each user's DNA data 304 comprises an encrypted text file. The encrypted file may have been created by third-party services 312 and transmitted to DNA information system 300 via the third-party service 312 or via user devices 310. The encrypted file contains all of a user's DNA data 304. Table header row 468 displays the different types of information contained in user raw data table 466 and table rows 468a, 468b, 468c, 468d, 468e, 468f, 468g, 468h, 468i, and 468j display the information for a particular user. As shown in FIG. 4H, table header row 468 includes fields for "User," "Filename," "Last Processed," and "Action." The "User" field corresponds to the last name of the user. The "Filename" field corresponds to the name of the encrypted file. As shown in table row 468d, the filename is "4zjhxf891da2.txt." The "Last Processed" field corresponds to the last time the encrypted file was parsed for DNA data 304 that is relevant to the user's endocannabinoid system. The "Action" field may include a selectable button that allows an administrator to initiate the parsing of an encrypted file for DNA data 304 most relevant to the user's endocannabinoid genotype. As discussed previously, this allows DNA information system 300 to better manage its network resources by only displaying the most relevant genetic information to the user.

Table rows 468a, 468b, 468c. 468d, 468e, 468f, 468g, 468h, 468i, and 468j include information relating to the information fields in table header row 468. For example, table row 468b has "Jones" for the "User" field, "29035798287.txt" for the "Filename" field, "2018-08-19 08:17:12" for the "Last Processed" field, and "Process File" for the "Action" field.

Table manipulator button 470 has the same functionality as table manipulator button 426 in FIG. 4B, table manipulator button 434 in FIG. 4C, and table manipulator button 448 in FIG. 4E. Specifically, table manipulator button 470 allows an administrator to manually add a user's DNA data to user raw data table 466. Table navigation button 472 has the same or similar functionality as table navigation button 428 in FIG. 4B and table navigation button 436 in FIG. 4C.

Figure 5A:
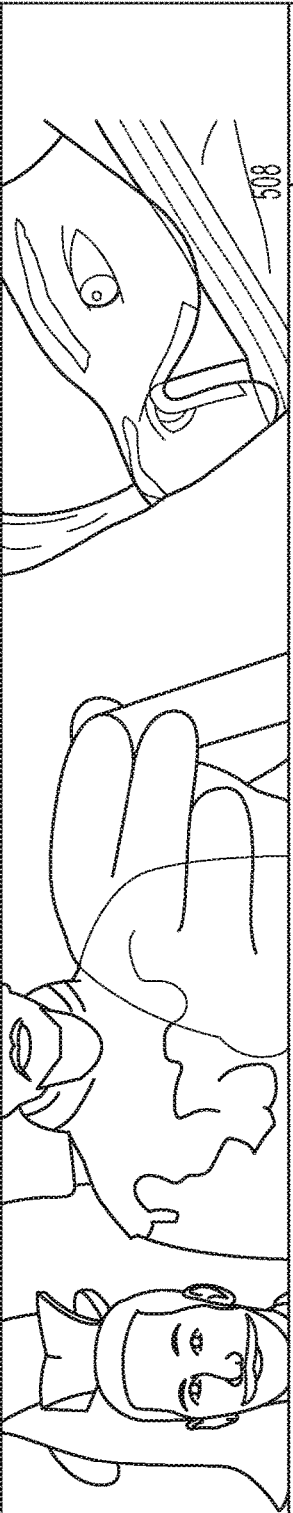
FIG. 5A depicts a graphical user interface showing DNA information at an end-user view, in accordance with example embodiments.
Figure 5C:
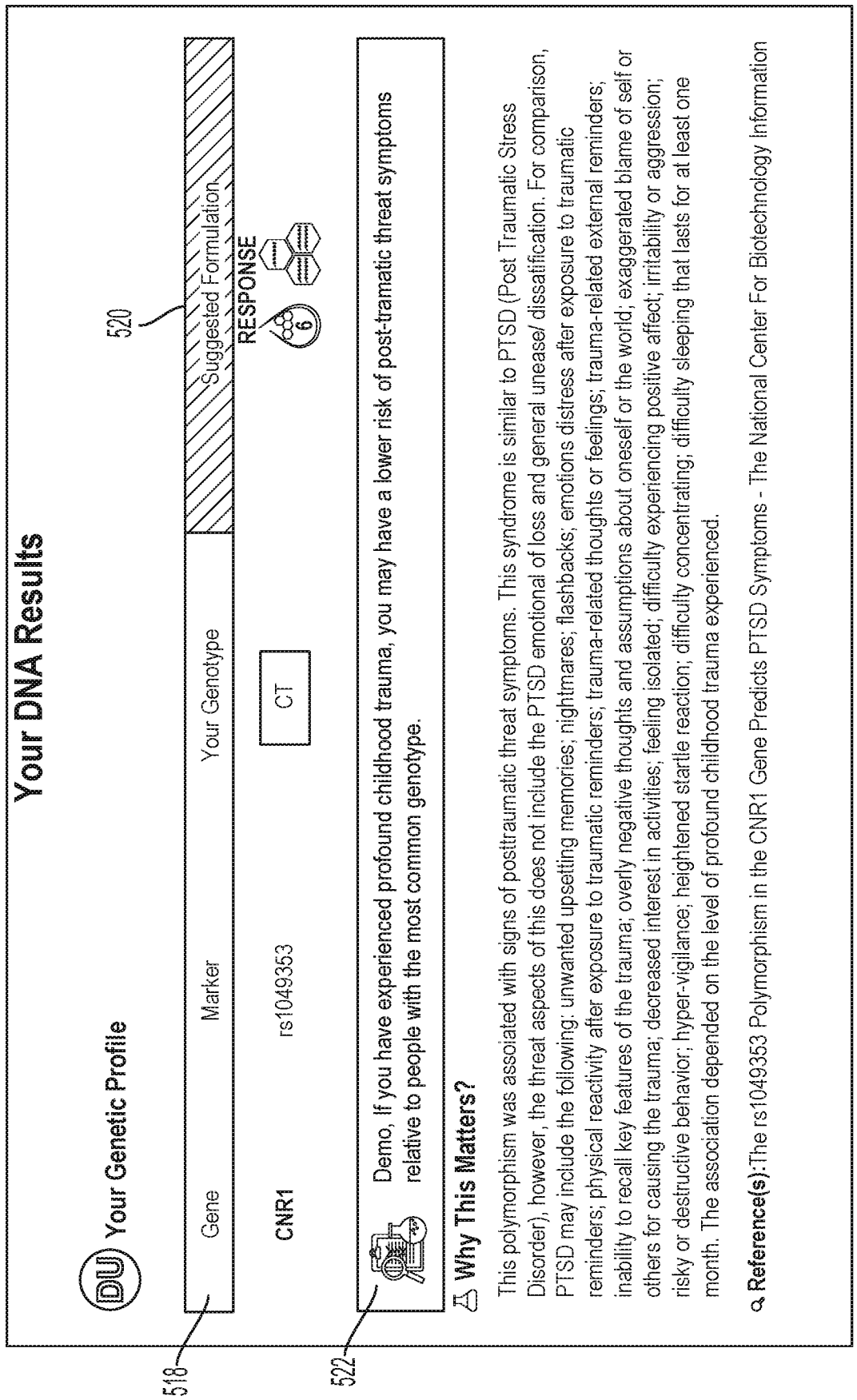
FIG. 5C depicts a graphical user interface also showing DNA information at the end-user view, in accordance with example embodiments.

FIGS. 5A-5C depict graphical user interfaces showing DNA information at a end-user view, in accordance with example embodiments. Each of these graphical user interfaces may be provided for display on a client device. The information provided therein may be derived, at least in part, from DNA data 304 stored in a database that is part of DNA information system 300. Nonetheless, these graphical user interfaces are merely for purpose of illustration. The applications described herein may provide a graphical user interface that formats information differently, includes more or less information, and includes different types of information.

When reference is made to DNA information being displayed an end-user view, it means the information is being transmitted to, and viewed by, an end-user. The end-user may access the graphical user interfaces via user devices 310. This may be beneficial as it allows the end-user to view their DNA information in a portable, on-the-go format, which may in turn allow them to select appropriate cannabinoid formulations without having to bring a physical endocannabinoid DNA report.

FIG. 5A depicts a graphical user interface 500 at a end-user view. In FIG. 5A, graphical user interface 500 includes navigation tabs 502, report list 504, user information 506, and report information 508.

Navigation tabs 502 are configured to assist a user in navigating graphical user interface 500. For example, as shown in FIG. 5A, navigation tabs 502 are selectable and include a tab for "Home," "Reports," "Wellness Plans," and "Articles." For example, selecting "Home" returns a user to the home screen illustrated in FIG. 5A. In another example, selecting "Reports" displays a drop down menu allowing a user to select which report he or she wants to view. In yet another example, selecting "Articles" may display a list of educational articles the user can read to learn more about the generated reports.

Report list 504 is configured to display the reports available to a user. As shown in FIG. 5A, the user has access to an overview of her reports and an Endocannabinoid DNA report. While these are the only reports shown, additional reports may be added by an administrator via reports table 444 in FIG. 4E.

User information 506 includes the account information for the user that is logged in. For example, selecting user information 506 may provide options to view a profile associated with the user and/or a selectable button to log out of the current user account.

Report information 508 includes a textual description of the report selected. As shown in FIG. 5A, the textual description includes overview information of the reports available to the user. For example, report information 508 describes the origin of *cannabis* as an introduction to the user's endocannabinoid DNA report.

In operation, selection of "Endocannabinoid DNA" in report list 504 or "Reports" in navigation tabs 502 will cause graphical user interface 500 to display the user's endocannabinoid DNA report.

FIG. 5B depicts a graphical user interface 500 at the end-user view. In FIG. 5B, graphical user interface 500 includes navigation tabs 502, user information 506, report header 510, and report sections 512, 514, and 516. Navigation tabs 502 operate the same across all of FIGS. 5A-5C.

Report header 510 corresponds to the type of endocannabinoid genetic marker being displayed in graphical user interface 500. For example, as shown in FIG. 5B, report header 510 corresponds to genetic markers related to mental health and wellness. In another example, report header 510 may correspond to genetic markers related to physical health and wellness.

Report sections 512, 514, and 516 display information related to a number of genetic markers related to mental health and wellness. For example, in FIG. 5B, report section 512 corresponds to anxiety, report section 514 corresponds to bipolar disorder, and report section 516 corresponds to cognitive function. The full list of genetic markers that may be displayed in report sections 512, 514, and 516 are described above in Section IV: Example Endocannabinoid Genotype Markers. Report sections 512, 514, and 516 may be selectable by a user to display detailed information regarding the selected genetic marker.

In operation, if a user wants to learn more about the genetic marker anxiety and how it related to her own DNA, the user may select report section 512, which corresponds to anxiety in FIG. 5B.

FIG. 5C depicts a graphical user interface 500 at the end-user view. In FIG. 5C, graphical user interface 500 includes genetic information 518, suggestion formulation 520, and personal assessment 522.

Genetic information 518 may include information parsed from the user's DNA data 304, including a gene identifier, genetic marker (e.g., SNP), and the user's genotype. For example, as shown in FIG. 5C, genetic information 518 references the rs1049353 SNP of the CNR1 gene and also indicates the user has heterozygous alleles (C/T) for this polymorphism.

Suggestion formulation 520 is a suggested cannabinoid formulation that is part of the recommendation generated by recommendation engine 306 of DNA information system 300. For example, because the user in FIG. 5C has heterozygous alleles (C/T) for the rs1049353 polymorphism of the CNR1 gene, the suggested formulation is a cannabinoid formulation with an 18:1 to 4:1 CBD to THC ratio, with linalool as the primary terpene, and β-caryophyllene as the secondary terpene. This formulation is most effective in *cannabis* users that have high anxiety. A list of suggested cannabinoid formulations can be found in U.S. Provisional Patent Application No. 62/680,885, the contents of which are incorporated by reference herein.

Personal assessment 522 is an assessment generated for a user based on their genotype in relation to the polymorphism of the gene. In FIG. 5C, personal assessment 522 states "If you have experienced profound childhood trauma, you may have a lower risk of post-traumatic threat symptoms relative to people with the most common genotype." This information may be particularly relevant to a use that has experienced childhood trauma as it may assist the user in selecting an appropriate cannabinoid formulation.

The graphical user interfaces of FIGS. 4A-4H and 5A-5C are examples, and different graphical user interfaces with different arrangements of information could be used and are contemplated herein.

VI. EXAMPLE OPERATIONS

Figure 6:
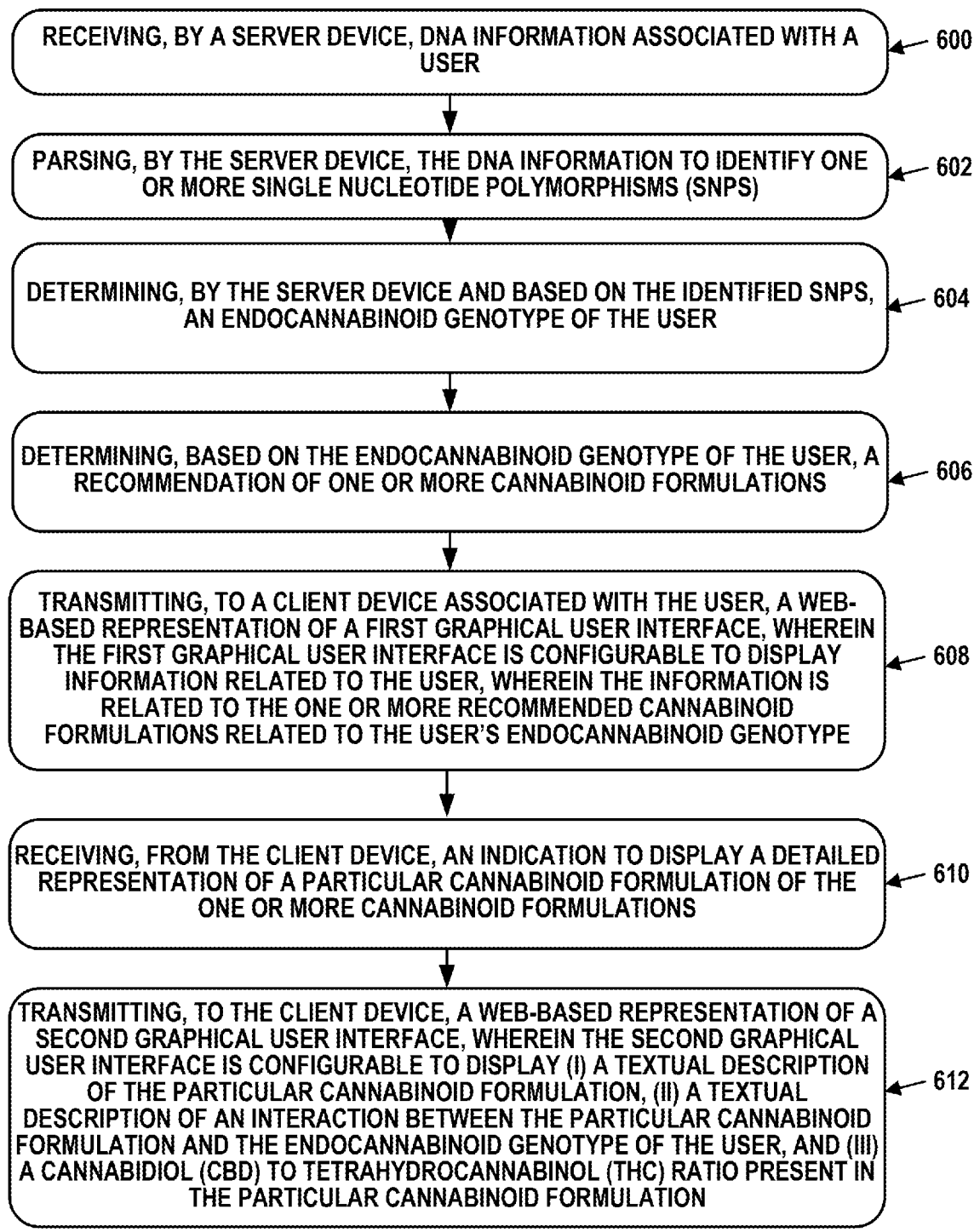
FIG. 6 is a flow chart, in accordance with example embodiments.

FIG. 6 is a flow chart illustrating an example embodiment. The process illustrated by FIG. 6 may be carried out by a computing device, such as computing device 100, and/or a cluster of computing devices, such as server cluster 200. However, the process can be carried out by other types of devices or device subsystems. For example, the process could be carried out by a portable computer, such as a laptop or a tablet device.

The embodiments of FIG. 6 may be simplified by the removal of any one or more of the features shown therein. Further, these embodiments may be combined with features, aspects, and/or implementations of any of the previous figures or otherwise described herein.

Block 600 may involve receiving, by a server device, DNA information associated with a user.

Block 602 may involve parsing, by the server device, the DNA information to identify one or more single nucleotide polymorphisms (SNPs).

Block 604 may involve determining, by the server device and based on the identified SNPs an endocannabinoid genotype of the user.

Block 606 may involve determining, based on the endocannabinoid genotype of the user, a recommendation of one or more cannabinoid formulations.

Block 608 may involve transmitting, to a client device associated with the user, a web-based representation of a first graphical user interface. The first graphical user interface is configurable to display information related to the user. The information is related to the one or more recommended cannabinoid formulations related to the endocannabinoid genotype of the user.

Block 610 may involve receiving, from the client device, an indication to display a detailed representation of a particular cannabinoid formulation of the one or more cannabinoid formulations.

Block 612 may involve transmitting, to the client device, a web-based representation of a second graphical user interface. The second graphical user interface is configurable to display (i) a textual description of the particular cannabinoid formulation, (ii) a textual description of an interaction between the particular cannabinoid formulation and the endocannabinoid genotype of the user, and (iii) a cannabidiol (CBD) to tetrahydrocannabinol (THC) ratio present in the particular cannabinoid formulation.

Some embodiments may further involve receiving, from the client device, an indication to display a detailed representation of a particular genetic disorder, and transmitting, to the client device, a web-based representation of a third graphical user interface, wherein the third graphical user interface is configurable to display a textual description of (i) the particular genetic disorder and (ii) how the particular genetic disorder is related to the endocannabinoid genotype of the user.

In some embodiments, the second graphical user interface is further configurable to display a personalized assessment to the user.

In some embodiments, receiving, by the server device, the DNA information associated with a user comprises receiving a DNA test kit from the user.

In some embodiments, receiving, by the server device, the DNA information associated with a user comprises receiving the DNA information from a third-party laboratory.

In some embodiments, parsing, by the server device, the DNA information to identify one or more SNPs comprises removing the DNA information that is not associated with the endocannabinoid genotype of the user.

In some embodiments, receiving, by the server device, the DNA information associated with a user comprises receiving the DNA information from a third-party DNA information provider.

VII. CONCLUSION

The present disclosure is not to be limited in terms of the particular embodiments described in this application, which are intended as illustrations of various aspects. Many modifications and variations can be made without departing from its scope, as will be apparent to those skilled in the art. Functionally equivalent methods and apparatuses within the scope of the disclosure, in addition to those described herein, will be apparent to those skilled in the art from the foregoing descriptions. Such modifications and variations are intended to fall within the scope of the appended claims.

The above detailed description describes various features and operations of the disclosed systems, devices, and methods with reference to the accompanying figures. The example embodiments described herein and in the figures are not meant to be limiting. Other embodiments can be utilized, and other changes can be made, without departing from the scope of the subject matter presented herein. It will be readily understood that the aspects of the present disclosure, as generally described herein, and illustrated in the figures, can be arranged, substituted, combined, separated, and designed in a wide variety of different configurations.

With respect to any or all of the message flow diagrams, scenarios, and flow charts in the figures and as discussed herein, each step, block, and/or communication can represent a processing of information and/or a transmission of information in accordance with example embodiments. Alternative embodiments are included within the scope of these example embodiments. In these alternative embodiments, for example, operations described as steps, blocks, transmissions, communications, requests, responses, and/or messages can be executed out of order from that shown or discussed, including substantially concurrently or in reverse order, depending on the functionality involved. Further, more or fewer blocks and/or operations can be used with any of the message flow diagrams, scenarios, and flow charts discussed herein, and these message flow diagrams, scenarios, and flow charts can be combined with one another, in part or in whole.

A step or block that represents a processing of information can correspond to circuitry that can be configured to perform the specific logical functions of a herein-described method or technique. Alternatively or additionally, a step or block that represents a processing of information can correspond to a module, a segment, or a portion of program code (including related data). The program code can include one or more instructions executable by a processor for implementing specific logical operations or actions in the method or technique. The program code and/or related data can be stored on any type of computer readable medium such as a storage device including RAM, a disk drive, a solid state drive, or another storage medium.

The computer readable medium can also include non-transitory computer readable media such as computer readable media that store data for short periods of time like register memory and processor cache. The computer readable media can further include non-transitory computer readable media that store program code and/or data for longer periods of time. Thus, the computer readable media may include secondary or persistent long term storage, like ROM, optical or magnetic disks, solid state drives, compact-disc read only memory (CD-ROM), for example. The computer readable media can also be any other volatile or non-volatile storage systems. A computer readable medium can be considered a computer readable storage medium, for example, or a tangible storage device.

Moreover, a step or block that represents one or more information transmissions can correspond to information transmissions between software and/or hardware modules in the same physical device. However, other information transmissions can be between software modules and/or hardware modules in different physical devices.

The particular arrangements shown in the figures should not be viewed as limiting. It should be understood that other embodiments can include more or less of each element shown in a given figure. Further, some of the illustrated elements can be combined or omitted. Yet further, an example embodiment can include elements that are not illustrated in the figures.

While various aspects and embodiments have been disclosed herein, other aspects and embodiments will be apparent to those skilled in the art. The various aspects and embodiments disclosed herein are for purpose of illustration and are not intended to be limiting, with the true scope being indicated by the following claims.

What is claimed is:

1. A method comprising:
receiving, by a server device, deoxyribonucleic acid (DNA) information associated with a user, wherein the received DNA information is in a first raw DNA data format;
parsing, by the server device, the DNA information to identify one or more single nucleotide polymorphisms (SNPs) that are indicative of the user's interactions with cannabinoid formulations;
extracting, by the server device, the identified one or more SNPs from the DNA information in the first raw DNA data format;
storing, by the server device, the extracted one or more SNPs in a second parsed DNA data format;
determining, by the server device and based on the extracted one or more SNPs, an endocannabinoid genotype of the user;
accessing, by the server device, a database identifying (i) a plurality of endocannabinoid genotypes and (ii) a plurality of cannabinoid formulations, wherein each endocannabinoid genotype of the plurality of endocannabinoid genotypes is associated with one or more cannabinoid formulations of the plurality of cannabinoid formulations;
determining, by the server device, a recommendation of a particular cannabinoid formulation of the plurality of cannabinoid formulations based on the particular cannabinoid formulation being associated in the database with the determined endocannabinoid genotype of the user;
transmitting, to a client device associated with the user, a web-based representation of a first graphical user interface, wherein the first graphical user interface is configurable to display information related to the user, wherein the information is related to the particular cannabinoid formulations and the endocannabinoid genotype of the user;
receiving, from the client device, an indication to display a detailed representation of the particular cannabinoid formulation; and
transmitting, to the client device, a web-based representation of a second graphical user interface, wherein the second graphical user interface is configurable to display (i) a textual description of the particular cannabinoid formulation, (ii) a textual description of an interaction between the particular cannabinoid formulation and the endocannabinoid genotype of the user, and (iii) a cannabidiol (CBD) to tetrahydrocannabinol (THC) ratio present in the particular cannabinoid formulation.

2. The method of claim 1, further comprising:
receiving, from the client device, an indication to display a detailed representation of a particular genetic disorder; and
transmitting, to the client device, a web-based representation of a third graphical user interface, wherein the third graphical user interface is configurable to display a textual description of (i) the particular genetic disorder and (ii) how the particular genetic disorder is related to the endocannabinoid genotype of the user.

3. The method of claim 1, wherein the second graphical user interface is further configurable to display a personalized assessment to the user.

4. The method of claim 1, wherein receiving, by the server device, the DNA information associated with a user comprises receiving results of a DNA test kit supplied by the user.

5. The method of claim 1, wherein receiving, by the server device, the DNA information associated with a user comprises receiving the DNA information from a third-party laboratory.

6. The method of claim 1, wherein extracting, by the server device, the identified one or more SNPs from the DNA information comprises removing the DNA information that is not associated with the endocannabinoid genotype of the user.

7. The method of claim 1, wherein receiving, by the server device, the DNA information associated with a user comprises receiving the DNA information from a third-party DNA information provider.

8. An article of manufacture including a non-transitory computer-readable medium, having stored thereon program instructions that, upon execution by a computing device, cause the computing device to perform operations comprising:
receiving deoxyribonucleic acid (DNA) information associated with a user, wherein the received DNA information is in a first raw DNA data format;
parsing the DNA information to identify one or more single nucleotide polymorphisms (SNPs) that are indicative of the user's interactions with cannabinoid formulations;
extracting the identified one or more SNPs from the DNA information in the first raw DNA data format;
storing the extracted one or more SNPs in a second parsed DNA data format;
determining, based on the extracted one or more SNPs, an endocannabinoid genotype of the user;
accessing a database identifying (i) a plurality of endocannabinoid genotypes and (ii) a plurality of cannabinoid formulations, wherein each endocannabinoid genotype of the plurality of endocannabinoid genotypes is associated with one or more cannabinoid formulations of the plurality of cannabinoid formulations;
determining a recommendation of a particular cannabinoid formulation of the plurality of cannabinoid formulations based on the particular cannabinoid formulation being associated in the database with the determined endocannabinoid genotype of the user;
transmitting, to a client device associated with the user, a web-based representation of a first graphical user interface, wherein the first graphical user interface is configurable to display information related to the user, wherein the information is related to the particular cannabinoid formulations and the endocannabinoid genotype of the user;

receiving, from the client device, an indication to display a detailed representation of the particular cannabinoid formulation; and transmitting, to the client device, a web-based representation of a second graphical user interface, wherein the second graphical user interface is configurable to display (i) a textual description of the particular cannabinoid formulation, (ii) a textual description of an interaction between the particular cannabinoid formulation and the endocannabinoid genotype of the user, and (iii) a cannabidiol (CBD) to tetrahydrocannabinol (THC) ratio present in the particular cannabinoid formulation.

9. The article of manufacture of claim 8, further comprising:

receiving, from the client device, an indication to display a detailed representation of a particular genetic disorder; and transmitting, to the client device, a web-based representation of a third graphical user interface, wherein the third graphical user interface is configurable to display a textual description of (i) the particular genetic disorder and (ii) how the particular genetic disorder is related to the endocannabinoid genotype of the user.

10. The article of manufacture of claim 8, wherein the second graphical user interface is further configurable to display a personalized assessment to the user.

11. The article of manufacture of claim 8, wherein receiving the DNA information associated with a user comprises receiving results of a DNA test kit supplied by the user.

12. The article of manufacture of claim 8, wherein receiving the DNA information associated with a user comprises receiving the DNA information from a third-party laboratory.

13. The article of manufacture of claim 8, wherein extracting the identified one or more SNPs from the DNA information comprises removing the DNA information that is not associated with the endocannabinoid genotype of the user.

14. A computing device comprising:
at least one processor;
memory; and
program instructions, stored in the memory, that upon execution by the at least one processor cause the computing device to perform operations comprising:
receiving deoxyribonucleic acid (DNA) information associated with a user, wherein the received DNA information is in a first raw DNA data format;
parsing the DNA information to identify one or more single nucleotide polymorphisms (SNPs) that are indicative of the user's interactions with cannabinoid formulations;
extracting the identified one or more SNPs from the DNA information in the first raw DNA data format;
storing the extracted one or more SNPs in a second parsed DNA data format;
determining, based on the extracted one or more SNPs, an endocannabinoid genotype of the user;
accessing a database identifying (i) a plurality of endocannabinoid genotypes and (ii) a plurality of cannabinoid formulations, wherein each endocannabinoid genotype of the plurality of endocannabinoid genotypes is associated with one or more cannabinoid formulations of the plurality of cannabinoid formulations;
determining a recommendation of a particular cannabinoid formulation of the plurality of cannabinoid formulations based on the particular cannabinoid formulation being associated in the database with the determined endocannabinoid genotype of the user;
transmitting, to a client device associated with the user, a web-based representation of a first graphical user interface, wherein the first graphical user interface is configurable to display information related to the user, wherein the information is related to the particular cannabinoid formulation and the endocannabinoid genotype of the user;
receiving, from the client device, an indication to display a detailed representation of the particular cannabinoid formulation; and
transmitting, to the client device, a web-based representation of a second graphical user interface, wherein the second graphical user interface is configurable to display (i) a textual description of the particular cannabinoid formulation, (ii) a textual description of an interaction between the particular cannabinoid formulation and the endocannabinoid genotype of the user, and (iii) a cannabidiol (CBD) to tetrahydrocannabinol (THC) ratio present in the particular cannabinoid formulation.

15. The computing device of claim 14, wherein performing the operations further comprise:
receiving, from the client device, an indication to display a detailed representation of a particular genetic disorder; and
transmitting, to the client device, a web-based representation of a third graphical user interface, wherein the third graphical user interface is configurable to display a textual description of (i) the particular genetic disorder and (ii) how the particular genetic disorder is related to the endocannabinoid genotype of the user.

16. The computing device of claim 14, wherein the second graphical user interface is further configurable to display a personalized assessment to the user.

17. The computing device of claim 14, wherein receiving the DNA information associated with a user comprises receiving results of a DNA test kit supplied by the user.

18. The computing device of claim 14, wherein receiving the DNA information associated with a user comprises receiving the DNA information from a third-party laboratory.

19. The computing device of claim 14, wherein extracting the identified one or more SNPs from the DNA information comprises removing the DNA information that is not associated with the endocannabinoid genotype of the user.

20. The computing device of claim 14, wherein receiving the DNA information associated with a user comprises receiving the DNA information from a third-party DNA information provider.

* * * * *